US012605520B2

(12) United States Patent
Fine et al.

(10) Patent No.: US 12,605,520 B2
(45) Date of Patent: Apr. 21, 2026

(54) DELIVERY OF ULTRA PURE NITRIC OXIDE (NO)

(71) Applicant: VERO BIOTECH INC., Atlanta, GA (US)

(72) Inventors: David H. Fine, Cocoa Beach, FL (US);
Gregory Vasquez, Cocoa, FL (US);
Bryan Johnson, Orlando, FL (US);
Ryan Denton, Central City, CO (US);
Lucas G. Gamero, Oviedo, FL (US)

(73) Assignee: VERO Biotech Inc., Atlanta, GA (US)

( * ) Notice: Subject to any disclaimer, the term of this patent is extended or adjusted under 35 U.S.C. 154(b) by 488 days.

(21) Appl. No.: 18/184,847

(22) Filed: Mar. 16, 2023

(65) Prior Publication Data

US 2023/0398323 A1 Dec. 14, 2023

Related U.S. Application Data

(63) Continuation of application No. 16/247,516, filed on Jan. 14, 2019, now Pat. No. 11,607,520, which is a
(Continued)

(51) Int. Cl.
*A61M 16/12* (2006.01)
*A61M 16/10* (2006.01)
(Continued)

(52) U.S. Cl.
CPC .......... *A61M 16/122* (2014.02); *A61M 16/10* (2013.01); *A61M 16/12* (2013.01);
(Continued)

(58) Field of Classification Search
CPC ........ A24F 15/015; A24F 40/10; A24F 40/42; A24F 40/48; A24F 40/485; A61B 18/042;
(Continued)

(56) References Cited

U.S. PATENT DOCUMENTS 2,799,159 A 7/1957 Sabol
3,393,047 A 7/1968 Steinmetz-Schmaltz
(Continued)

FOREIGN PATENT DOCUMENTS

WO 9210228 A 6/1992
WO 9317741 A1 9/1993
(Continued)

OTHER PUBLICATIONS

Examination Report No. 1 for Australian Application No. 2011245476, dated Jul. 29, 2014, 3 pages.
(Continued)

*Primary Examiner* — Annette Dixon
(74) *Attorney, Agent, or Firm* — Meunier Carlin & Curfman LLC

(57) ABSTRACT

A system for delivering a therapeutic amount of nitric oxide can include a reservoir including a restrictor with a length of at least 0.5 inches and at most 2 inches covered by a metal sheath, a gas supply, and a delivery conduit. A delivery conduit can include at least one cartridge and a patient interface. The at least one cartridge can include a surface-active material and a reducing agent.

15 Claims, 18 Drawing Sheets

Related U.S. Application Data continuation of application No. 14/546,373, filed on Nov. 18, 2014, now Pat. No. 10,179,222, which is a continuation of application No. 13/094,535, filed on Apr. 26, 2011, now Pat. No. 8,887,720.

(60) Provisional application No. 61/328,010, filed on Apr. 26, 2010.

(51) Int. Cl.

| *C01B 21/24* | (2006.01) |
| *A61M 16/00* | (2006.01) |
| *A61M 16/06* | (2006.01) |

(52) U.S. Cl.

CPC ..... *C01B 21/24* (2013.01); *A61M 2016/0027* (2013.01); *A61M 16/0666* (2013.01); *A61M 2016/102* (2013.01); *A61M 16/105* (2013.01); *A61M 16/1055* (2013.01); *A61M 16/107* (2014.02); *A61M 16/1075* (2013.01); *A61M 2202/0266* (2013.01); *A61M 2202/0275* (2013.01); *A61M 2202/03* (2013.01); *A61M 2205/0238* (2013.01); *A61M 2205/18* (2013.01); *A61M 2205/3368* (2013.01); *A61M 2205/3653* (2013.01); *A61M 2205/7518* (2013.01); *A61M 2205/8206* (2013.01); *A61M 2207/10* (2013.01); *A61M 2209/088* (2013.01)

(58) Field of Classification Search

CPC ....... A61B 5/087; A61B 5/6819; A61B 7/003; A61D 7/04; A61F 13/0226; A61F 13/05; A61F 13/8405; A61F 2013/00646; A61F 2013/0091; A61G 10/00; A61G 10/04; A61G 11/00; A61G 2210/30; A61H 2033/143; A61H 2201/165; A61H 33/14; A61J 3/08; A61K 2300/00; A61K 31/04; A61K 31/198; A61K 33/00; A61K 33/24; A61K 33/30; A61K 33/34; A61K 9/007; A61K 9/2031; A61K 9/205; A61K 9/7007; A61L 15/44; A61L 2/0094; A61L 2209/132; A61L 2300/114; A61L 2300/60; A61L 9/12; A61M 11/005; A61M 11/007; A61M 11/008; A61M 11/042; A61M 13/003; A61M 15/00; A61M 15/0016; A61M 15/0025; A61M 15/0071; A61M 15/008; A61M 15/0098; A61M 15/02; A61M 15/025; A61M 15/06; A61M 15/08; A61M 16/00; A61M 16/0051; A61M 16/0057; A61M 16/0063; A61M 16/0066; A61M 16/009; A61M 16/0096; A61M 16/021; A61M 16/024; A61M 16/06; A61M 16/0666; A61M 16/0672; A61M 16/0677; A61M 16/0808; A61M 16/0816; A61M 16/0833; A61M 16/085; A61M 16/0866; A61M 16/10; A61M 16/1005; A61M 16/104; A61M 16/105; A61M 16/1055; A61M 16/106; A61M 16/107; A61M 16/1075; A61M 16/109; A61M 16/12; A61M 16/122; A61M 16/125; A61M 16/16; A61M 16/161; A61M 16/20; A61M 16/202; A61M 16/203; A61M 16/204; A61M 16/208; A61M 16/209; A61M 2005/14204; A61M 2005/14513; A61M 2005/2026; A61M 2016/0021; A61M 2016/0024; A61M 2016/0027; A61M 2016/003; A61M 2016/0033; A61M 2016/0039; A61M 2016/0042; A61M 2016/102; A61M 2016/1025; A61M 2016/1035; A61M 2202/0007; A61M 2202/0078; A61M 2202/0208; A61M 2202/0266; A61M 2202/0275; A61M 2202/03; A61M 2202/062; A61M 2205/0238; A61M 2205/07; A61M 2205/12; A61M 2205/123; A61M 2205/15; A61M 2205/18; A61M 2205/3306; A61M 2205/3317; A61M 2205/3324; A61M 2205/3334; A61M 2205/3368; A61M 2205/3375; A61M 2205/3569; A61M 2205/3592; A61M 2205/3613; A61M 2205/3653; A61M 2205/368; A61M 2205/42; A61M 2205/50; A61M 2205/581; A61M 2205/583; A61M 2205/584; A61M 2205/6018; A61M 2205/6027; A61M 2205/707; A61M 2205/7518; A61M 2205/7545; A61M 2205/8206; A61M 2205/8225; A61M 2205/8231; A61M 2205/8237; A61M 2207/10; A61M 2209/06; A61M 2209/088; A61M 2210/0681; A61M 35/30; A61M 5/14244; A61M 5/14526; A61M 5/19; A61M 5/2046; A61N 1/44; A61P 1/08; A61P 11/00; A61P 11/06; A61P 11/08; A61P 17/00; A61P 25/04; A61P 25/20; A61P 3/00; A61P 31/04; A61P 43/00; A61P 7/00; A61P 9/00; A61P 9/08; A61P 9/10; A61P 9/12; A62B 19/00; A62B 21/00; A62B 7/08; B01D 2253/104; B01D 2253/106; B01D 2253/108; B01D 2257/302; B01D 2257/402; B01D 2257/404; B01D 2259/40084; B01D 2259/401; B01D 2259/402; B01D 2259/4143; B01D 2259/4533; B01D 53/04; B01D 53/0415; B01D 53/0446; B01D 53/46; B01D 53/56; B01D 53/565; B01D 53/8625; B01F 23/12; B01J 12/007; B01J 19/088; B01J 20/26; B01J 2219/0801; B01J 2219/0809; B01J 2219/0871; B01J 2219/0875; B01J 2219/0894; B05B 11/025; B05B 11/04; B05B 11/061; B05B 7/0012; B05B 7/1686; C01B 21/1472; C01B 21/24; C01B 21/26; C01B 21/30; C01B 21/32; C01B 23/0047; C02F 1/70; C08L 71/123; C25B 1/00; G01N 1/28; G01N 27/416; G01N 33/0006; G05D 11/035; H05B 1/0244; H05B 2203/021; H05B 2203/022; H05H 1/48; H05H 2245/30; Y02A 50/20; Y02C 20/10; Y02E 60/10; Y10S 422/904; Y10S 55/35; Y10S 95/90; Y10T 137/7808; Y10T 436/179228

See application file for complete search history.

(56) References Cited

U.S. PATENT DOCUMENTS

| | | | |
|---|---|---|---|
| 3,856,204 A | 12/1974 | Chand |
| 3,903,883 A | 9/1975 | Pecina et al. |
| 4,399,942 A | 8/1983 | Chand |
| 4,621,632 A | 11/1986 | Bartels et al. |
| 4,676,237 A | 6/1987 | Wood et al. |
| 4,717,675 A | 1/1988 | Sievers |

(56)                    References Cited

U.S. PATENT DOCUMENTS

| | | | |
|---|---|---|---|
| 4,993,436 | A | 2/1991 | Bloom, Jr. |
| 5,062,145 | A | 10/1991 | Zwaan et al. |
| 5,108,705 | A | 4/1992 | Rounbehler et al. |
| 5,156,334 | A | 10/1992 | Kimbell et al. |
| 5,264,198 | A | 11/1993 | Grzyll |
| 5,336,156 | A | 8/1994 | Miller et al. |
| 5,365,776 | A | 11/1994 | Lehmann |
| 5,437,410 | A | 8/1995 | Babasade |
| 5,639,441 | A | 6/1997 | Sievers et al. |
| 5,692,495 | A * | 12/1997 | Sheu ..................... C01B 21/26 |
| | | | 423/403 |
| 5,938,985 | A | 8/1999 | Rodgers |
| 6,083,399 | A | 7/2000 | Jameson et al. |
| 6,095,134 | A | 8/2000 | Sievers et al. |
| 6,368,870 | B1 | 4/2002 | Harp |
| 6,581,599 | B1 | 6/2003 | Stenzler |
| 6,749,834 | B2 | 6/2004 | Fein et al. |
| 6,843,388 | B1 | 1/2005 | Hollars |
| 7,040,313 | B2 | 5/2006 | Fine |
| 7,165,546 | B2 | 1/2007 | Frankie et al. |
| 7,355,216 | B2 | 4/2008 | Yang et al. |
| 7,560,076 | B2 | 7/2009 | Rounbehler et al. |
| 7,618,594 | B2 | 11/2009 | Rounbehler et al. |
| 8,057,742 | B2 | 11/2011 | Rounbehler et al. |
| 8,066,904 | B2 | 11/2011 | Fine |
| 8,079,998 | B2 | 12/2011 | Hole et al. |
| 8,083,997 | B2 | 12/2011 | Rounbehler et al. |
| 8,226,916 | B2 | 7/2012 | Rounbehler et al. |
| 8,256,430 | B2 | 9/2012 | Torchia et al. |
| 8,371,296 | B2 | 2/2013 | Fine |
| 8,609,028 | B2 | 12/2013 | Rounbehler et al. |
| 8,887,720 | B2 | 11/2014 | Fine |
| 10,179,222 | B2 | 1/2019 | Fine |
| 11,000,484 | B2 | 5/2021 | Fine |
| 2003/0062043 | A1 * | 4/2003 | Fine ..................... A61K 33/00 |
| | | | 128/203.12 |
| 2006/0048779 | A1 * | 3/2006 | Rounbehler ............ A61P 17/00 |
| | | | 128/203.12 |
| 2006/0096596 | A1 | 5/2006 | Occhialini et al. |
| 2006/0180147 | A1 | 8/2006 | Rounbehler et al. |
| 2008/0257915 | A1 | 10/2008 | Wold |
| 2008/0317874 | A1 | 12/2008 | Fine et al. |
| 2009/0263578 | A1 | 10/2009 | Lindfors et al. |
| 2009/0285731 | A1 | 11/2009 | Rounbehler et al. |
| 2010/0003349 | A1 | 1/2010 | Miller |
| 2010/0043788 | A1 | 2/2010 | Fine et al. |
| 2012/0125328 | A1 | 5/2012 | Rounbehler et al. |

FOREIGN PATENT DOCUMENTS

| | | | |
|---|---|---|---|
| WO | 2008118360 | A1 | 10/2008 |
| WO | 2010021941 | A1 | 2/2010 |
| WO | 2010033916 | A1 | 3/2010 |
| WO | 2011063335 | A1 | 5/2011 |
| WO | 2011137124 | A1 | 11/2011 |

OTHER PUBLICATIONS

Extended European Search Report for European Application No. 11775504.1, mailed Jul. 3, 2015, 6 pages.

Extended European Search Report for European Application No. 20177876.8, mailed on Jan. 15, 2021, 8 pages.

International Search Report and Written Opinion for International Application No. PCT/US2011/033969 mailed Jul. 8, 2011, 9 pages.

Notice of Reasons for Refusal for Japanese Application No. 2013-508163, dated Dec. 19, 2014, 8 pages.

Notice of Reasons for Refusal for Japanese Application No. 2013-508163, dated Jul. 27, 2015, 8 pages.

Office Action for European Application No. 11775504.1, mailed Mar. 13, 2018, 5 pages.

* cited by examiner

501

801

DISPOSABLE

BASE UNIT

Air pump battery

Release button

DISPOSABLE IN BASE UNIT

DELIVERY OF ULTRA PURE NITRIC OXIDE (NO)

CLAIM OF PRIORITY

This application is a continuation of U.S. Application Ser. No. 16/247,516, filed on Jan. 14, 2019, which claims priority to U.S. application Ser. No. 14/546,373, filed on Nov. 18, 2014, which claims priority to U.S. application Ser. No. 13/094,535, filed on Apr. 26, 2011, which claims benefit of U.S. Provisional Application No. 61/328,010, filed on Apr. 26, 2010, each of which is incorporated by reference in its entirety.

TECHNICAL FIELD

This description relates to a systems and methods for the delivery of ultra pure nitric oxide.

BACKGROUND

Nitric oxide (NO), also known as nitrosyl radical, is a free radical that is an important signalling molecule. For example, NO can cause smooth muscles in blood vessels to relax, thereby resulting in vasodilation and increased blood flow through the blood vessel. These effects can be limited to small biological regions since NO can be highly reactive with a lifetime of a few seconds and can be quickly metabolized in the body.

Some disorders or physiological conditions can be mediated by inhalation of nitric oxide. The use of low concentrations of inhaled nitric oxide can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide can also be used to treat chronic pulmonary hypertension, bronchopulmonary dysplasia, chronic pulmonary thromboembolism and idiopathic or primary pulmonary hypertension or chronic hypoxia.

Generally, nitric oxide can be inhaled or otherwise delivered to the individual's lungs. Providing a therapeutic dose of NO could treat a patient suffering from a disorder or physiological condition that can be mediated by inhalation of NO or supplement or minimize the need for traditional treatments in such disorders or physiological conditions. Typically, the NO gas can be supplied in a bottled gaseous form diluted in nitrogen gas ($N_2$). Great care should be taken to prevent the presence of even trace amounts of oxygen ($O_2$) in the tank of NO gas because the NO, in the presence of $O_2$, can be oxidized to nitrogen dioxide ($NO_2$). Unlike NO, the part per million levels of $NO_2$ gas can be highly toxic if inhaled and can form nitric and nitrous acid in the lungs.

SUMMARY

In one aspect, a system for delivering a therapeutic amount of nitric oxide can include a reservoir, a gas supply and a delivery conduit. A reservoir can be configured to include a nitrogen dioxide source. A delivery conduit can include at least one cartridge. The at least one cartridge can include a surface-activated material and a reducing agent.

In another aspect, a reservoir assembly include a reservoir a restrictor.

In another aspect, a method of delivering nitric oxide can include releasing nitrogen dioxide from a reservoir into a delivery conduit via a restrictor, passing a gas from a gas supply into the delivery conduit which can allow the gas from the gas supply and the nitrogen dioxide to mix in the delivery conduit, passing the gas and nitrogen dioxide mixture through at least one cartridge, and delivering nitric oxide from an outlet of the delivery conduit.

In another aspect, a method of manufacturing a reservoir assembly for delivering nitric oxide can include coupling a restrictor to the reservoir, sealing a second end of the restrictor. The method can also include filling a reservoir with a source of nitrogen dioxide. Filling a reservoir can include filling a portion of the reservoir with a source of nitrogen dioxide. The method can further include inserting the restrictor into a metal tube that can be coupled to the reservoir via an adaptor, holding the restrictor place by graphite ferrules, heat sealing the restrictor, and/or testing the restrictor and/or assembly with a helium flow. The testing can be used to check for leaks prior to filling with liquid $N_2O_4$.

In some embodiments, a reservoir can include a nitrogen dioxide source. In some embodiments, the nitrogen dioxide source is dinitrogen tetroxide, more specifically, liquid dinitrogen tetroxide. The amount of liquid $N_2O_4$ in the reservoir can be less than about 5.0 g, less than about 2.0 g, less than about 1.0 g, less than about 0.50 g, less than 0.25 g or less than 0.10 g; the amount of liquid $N_2O_4$ in the reservoir can be greater than about 0.05 g, greater than about 0.10 g, greater than about 0.20 g, greater than about 0.50 g or greater than about 1.0 g. The amount of liquid $N_2O_4$ in the reservoir can be less than about 5 ml, less than about 2 ml, less than about 1 ml, less than about 0.5 ml, less than about 0.25 ml or less than about 0.10 ml; the amount of liquid $N_2O_4$ in the reservoir can be greater than about 0.001 ml, greater than about 0.01 ml, greater than about 0.05, greater than about 0.10 ml, greater than about 0.25 ml, greater than about 0.50 ml or greater than about 1.0 ml.

In some embodiments, the reservoir can include a restrictor. In some cases, the restrictor can be coupled to the reservoir.

In some embodiments, a reservoir can also include nitrogen dioxide vapor or nitrogen dioxide gas in a space over the nitrogen dioxide source.

In some embodiments, a reservoir can be less than 6 inches, less than 4 inches, less than 3 inches, less than 2 inches, less than 1 inch, less than 0.5 inch in height. A reservoir can also be less than 4 inches, less than 2 inches, less than 1 inch, less than 0.75 inch or less than 0.5 inch in internal diameter.

In some embodiments, a restrictor can include an orifice.

In some embodiments, a restrictor can include a first end and a second end. In some embodiments, the first end of the restrictor can be coupled to a reservoir. In some embodiments, the second end can be sealed or closed. In some embodiments, the second end, which was previously sealed or closed, can be opened, unsealed or include a broken seal. In some embodiments, the second end of the restrictor can also be coupled to the delivery conduit. In some embodiments, the delivery conduit can include a device for opening the second end or breaking the seal on the second end.

In some embodiments, a restrictor can further include a length corresponding to the distance between the first end and the second end. In some cases, the second end of the restrictor is coupled to the delivery conduit such that the delivery conduit traverses in a direction perpendicular to the length of the restrictor.

In some embodiments, the restrictor can include a tube. In some embodiments, the tube can be a capillary tube, more specifically, a quartz capillary tube. In some embodiments, the length of the restrictor can be at least about 0.1 inch, at least about 0.25 inch or at least about 0.5 inch; the length can be at most about 4 inches, at most about 2 inches, at most about 1 inch, or at most about 0.5 inch. Preferably, the restrictor can have a length of about 0.75 inch. In some embodiments, the internal diameter of the restrictor can be at least about 0.001, at least about 0.005 microns or at least about 0.010; the internal diameter can be at most about 0.100 microns, at most about 0.050 microns, at most about 0.025 microns, or at most about 0.010 microns. Preferably, the restrictor can have a diameter of about 0.010 microns.

In some embodiments, the gas supply can supply air, oxygen or nitrogen. In some circumstances, the gas supply can be an air supply, more specifically, an air pump. The air pump can be battery powered. The gas supplied by the gas supply can be moist or dry. In some embodiments, the gas supply can be in fluid communication with the delivery conduit.

In some embodiments, the delivery conduit can have an inlet coupled to the gas source. In some embodiments, the delivery conduit can also include an outlet. In some circumstances, the delivery conduit can include an outlet coupled to the patient interface. A patient interface can include a mouth piece, nasal cannula, face mask, or fully-sealed face mask.

In some embodiments, a cartridge can include a surface-activated material and a reducing agent. In some cases, the surface-activated material can be saturated with an aqueous solution of a reducing agent. Any appropriate reducing agent that can convert $NO_2$ or $N_2O_4$ to NO can be used as determined by a person of skill in the art. For example, the reducing agent can include a hydroquinone, glutathione, and/or one or more reduced metal salts such as Fe(II), Mo(VI), NaI, Ti(III) or Cr(III), thiols, or $NO_2^-$. The reducing agent can be an antioxidant. The antioxidant can be an aqueous solution of an antioxidant. The antioxidant can be ascorbic acid, alpha tocopherol, or gamma tocopherol. Any appropriate antioxidant can be used depending on the activities and properties as determined by a person of skill in the art. The antioxidant can be used dry or wet.

In some circumstances, the cartridge can also include an inlet and an outlet. The inlet can be configured to receive a gas flow that can include nitrogen dioxide and can fluidly communicate the gas flow to the outlet through the surface-active material, such that the surface-active material can react with nitrogen dioxide in the gas flow and can convert the nitrogen dioxide to nitric oxide.

In some embodiments, the delivery conduit further can include a second cartridge. The second cartridge can include a surface-activated material and a reducing agent. In some circumstances, the cartridge can also include an inlet and an outlet. The inlet can be configured to receive a gas flow that can include nitrogen dioxide and can fluidly communicate the gas flow to the outlet through the surface-active material, such that the surface-active material can react with nitrogen dioxide in the gas flow and can convert the nitrogen dioxide to nitric oxide.

In some embodiments, the system can include a disposable module and a base unit. In some embodiments, the disposable module can include the reservoir, the restrictor and the first cartridge. In some embodiments, the system can include a base unit, where the base unit can include a gas supply. In some embodiments, the base unit can include batteries, sensors and/or alarm electronics. In some embodiments, the base unit is reusable. In some embodiments, the disposable module can be attached to the base unit for delivery nitric oxide. In some circumstances, the disposable module is configured to be used or attached to the base unit only once.

In some embodiments, the method can further include comprising attaching a disposable module including a reservoir, a restrictor and a first cartridge to a base unit. The base unit can include the gas supply. The base unit can also include batteries, sensors and/or alarm electronics.

In some embodiments, a system can be portable. In some embodiments, a portable system can include a belt hook, belt, shoulder strap or other device for attaching a portable system to a person.

In some embodiments, the system can weigh less than 64 ounces, less than 32 ounces or less than 16 ounces. In some embodiments, the system can be less than 2 feet, less than 1.5 feet, less than 1 foot in height; the system can be less than 2 feet, less than 1.5 feet, less than 1 foot, less than 9 inches or less than 6 inches in width; and/or the system can be less than 6 inches, less than 4 inches, less than 3 inches or less than 2 inches in depth.

In some embodiments, a reservoir assembly can be less than 1 foot, less than 6 inches, less than 5 inches, less than 4 inches, less than 3 inches or less than 2 inches in height and/or less than 1 inch, less than 0.75 inch or less than 0.5 inch in diameter.

In some embodiments, the system can further include a nitric oxide sensor, a nitrogen dioxide sensor, a flow sensor, a pressure sensor, a sensor for atmospheric pressure, and/or a microbial filter.

In some embodiments, a system can further include a heating element. A heating element can include a hot water bath, a heating mantle, heating wire or heating well. A heating element can include a simple flexible circuit board with the wires etched onto the surface. In some cases, a device including a thermistor can be built into the circuit for measuring and controlling the temperature.

In some embodiments, the system can operate at a temperature of at least about 25° C., at least about 30° C., at least about 35° C., at least about 40° C., at least about 45° C. or at least about 50° C.; the system can operate at a temperature of at most about 200° C., at most about 150° C., at most about 100° C., or at most about 75° C. The optimum temperature range can be about 45 to 75° C.

In some embodiments, a method of delivering nitric oxide can include breaking the seal on or opening an end of the restrictor. Breaking the seal on or opening an end of the restrictor can allow nitrogen dioxide to traverse the length of the restrictor and out the previously closed or sealed end of the restrictor.

In some embodiments, a method of delivering nitric oxide can include heating a reservoir and/or restrictor to a temperature at least about 25° C., at least about 30° C., at least about 35° C., at least about 40° C., at least about 45° C. or at least about 50° C.; a method of delivering nitric oxide can include heating a reservoir and/or restrictor to a temperature at most about 200° C., at most about 150° C., at most about 100° C., or at most about 75° C. The optimum temperature range can be about 45 to 75° C. In some embodiments, releasing nitrogen dioxide from a reservoir into a restrictor and then into a delivery conduit can include heating a reservoir and/or restrictor. In some embodiments, heating a reservoir and/or restrictor can heat nitrogen dioxide in the reservoir, increasing the vapor pressure and releasing the nitrogen dioxide from releasing nitrogen dioxide from a reservoir into a restrictor and then into a delivery conduit.

In some embodiments, a reservoir assembly can include a heating element, which can reach and maintain a temperature of at least about 25° C., at least about 30° C., at least about 35° C., at least about 40° C., at least about 45° C. or at least about 50° C.; a reservoir assembly can include a heating element, which can reach and maintain a temperature of at most about 200° C., at most about 150° C., at most about 100° C. or at most about 75° C. The optimum temperature range can be about 45 to 75° C. In some embodiments, a method of manufacturing a reservoir assembly can include attaching a heating element, where the heating element can reach and maintain the temperatures discussed above.

DETAILED DESCRIPTION

When delivering nitric oxide (NO) for therapeutic use to a mammal, it can be important to avoid delivery of nitrogen dioxide (NO$_2$) to the mammal. Nitrogen dioxide (NO$_2$) can be formed by the oxidation of nitric oxide (NO) with oxygen (O$_2$). The rate of formation of nitrogen dioxide (NO$_2$) can be proportional to the oxygen (O$_2$) concentration multiplied by the square of the nitric oxide (NO) concentration—that is, (O$_2$)*(NO)*(NO)=NO$_2$. A NO delivery system can convert nitrogen dioxide (NO$_2$) to nitric oxide (NO).

Figure 1:
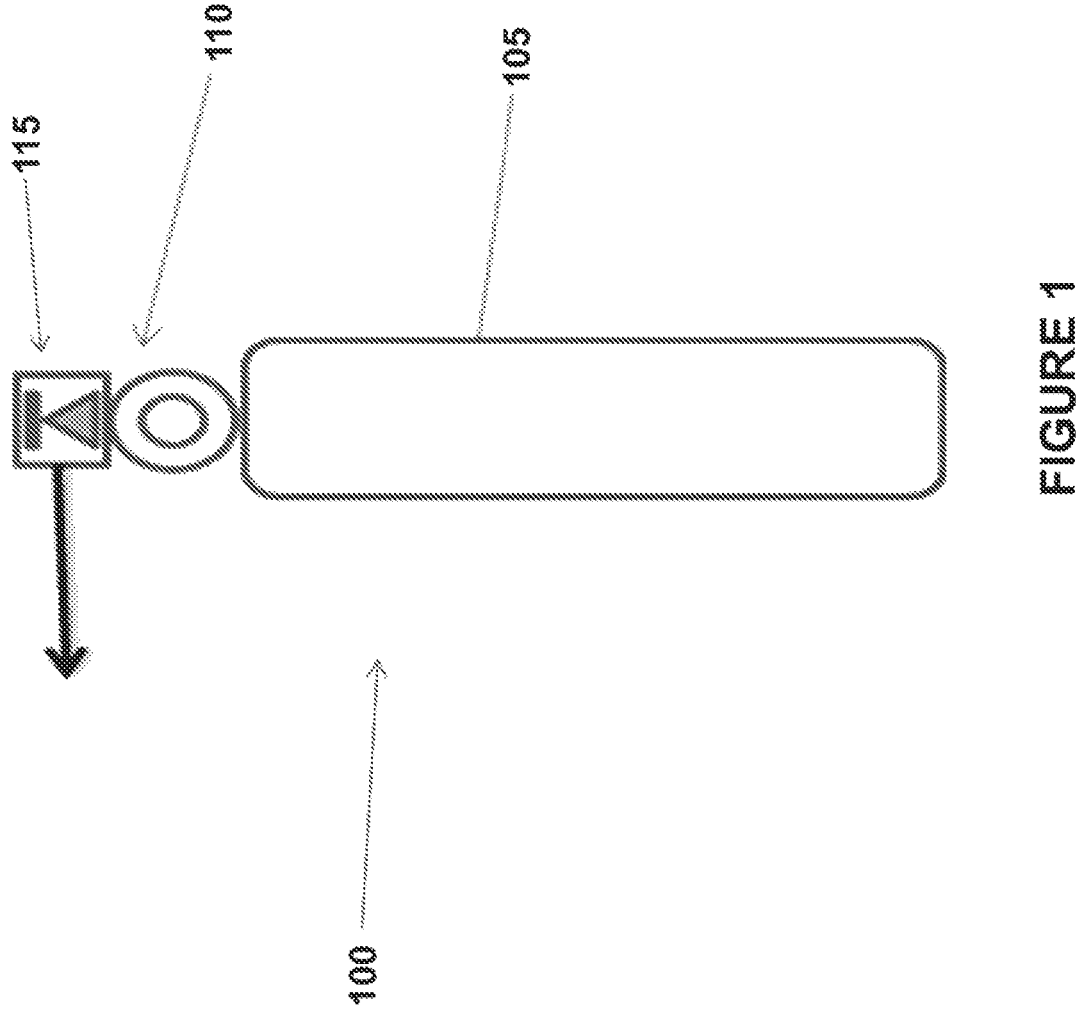
FIG. 1 is a diagram of a gas bottle platform.

Platforms for delivering nitric oxide currently exist. For example, a platform can be a standalone gas bottle platform, as shown in FIG. 1. A gas bottle platform 100 can include a gas bottle 105, a gas regulator 110 and a GeNO cartridge 115, for example. Using a gas bottle platform, the NO output can be defined by the nitrogen dioxide concentration in the gas bottle and cannot be varied by the user. For example, if the gas bottle contained 80 ppm of NO$_2$ in air or oxygen, then the output can be 80 ppm of NO$_2$ in air or oxygen. The gas can be supplied, typically, at a pressure of 2000 psi or greater. The output from the gas cylinder can be delivered to a GeNO cartridge, where one of the O atoms in the NO$_2$ is stripped out by a reducing agent, for example, ascorbic acid, to generate ultra pure NO. The GeNO cartridge is described in U.S. patent application Ser. Nos. 12/541,144 and 12/951,811, each of which is incorporated by reference in its entirety. This platform has been cleared by FDA for use in two clinical trials with human patients. A gas bottle platform can work well, but can be large, heavy and cumbersome because the platform can include a heavy aluminum or steel gas pressure cylinder, a gas regulator and a flow controller.

Another variation for delivering NO can be to start with a NO$_2$ gas concentration of up to 2,000 ppm in air or oxygen and dilute it down to 80 ppm of NO$_2$. This set up can be even more complex in that it can require precision mass flow controllers and meters in order to get a stable mixing ratio.

As mentioned above, the disadvantage of the gas bottle platform can be that the platform can be large and heavy. The platform can also be inconvenient to use for chronic treatment as an ambulatory platform. Gas bottles can also be cumbersome when used in a confined space such as in an Intensive Care Unit, in a hospital or in a home. In addition, the gas bottles need to be tied down to prevent them from falling over and causing physical injury. Also, the regulator can break off in a fall, and the sudden venting of gas through the opening can cause the heavy bottle to become a projectile, which can penetrate numerous walls and cause injury or death.

Examples of commercially available platforms are manufactured by Ikaria, two of which are the INOvent and the INOmax DS. Both of these systems use gas bottles of NO diluted in nitrogen (N$_2$), which is then mixed with oxygen enriched air to provide the inhaled NO gas. Both of these systems are designed to work with a ventilator in an intensive care setting in a hospital. These platforms are not suitable for ambulatory or home use.

Therefore, there is a need for a nitric oxide delivery platform, which can be used in settings where a large, heavy bottle platform is inconvenient, such as an ambulatory or home setting.

As one solution, a system can include a permeation tube or permeation cell to provide the source of NO$_2$. For example, the NO$_2$ source can be liquid dinitrogen tetroxide (N$_2$O$_4$). This approach has been shown to work well. This approach has been described in U.S. patent application Ser. No. 12/563,662, which is incorporated by reference in its entirety. N$_2$O$_4$ can vaporize to produce NO$_2$, and the process can be reversible. Using a permeation tube, air can be allowed to flow around the permeation tube, where it can mix with the NO$_2$ that diffuses through the tube, providing a stable mixture of NO$_2$ in air. The concentration of the NO$_2$ can be controlled by a number of factors including, for example, the temperature of the tube and the volume of the air flow. However, storing a permeation tube can be a problem. For instance, if NO$_2$ is in contact with the permeation tube polymer, the storage should be below –11° C. in order to keep the NO$_2$ frozen, which can prevent loss of NO$_2$. One solution is to build a separate storage chamber for the permeation tube, which can be connected to the storage tube by a simple valve. This device can be stored at room temperature without loss of NO$_2$, and it can easily be activated by connecting the reservoir to the permeation tube. The combined storage vessel and permeation tube can work well, but it can have one major disadvantage. Stabilization of a permeation tube can take a long time when the NO$_2$ is stored in a reservoir and then suddenly opened to the permeation tube. The time to stabilize can be several days.

Pre-saturating the permeation tube with $NO_2$ first can speed up the stabilization, but this may not work well with long term storage of months or years.

As another solution, a reservoir assembly can be utilized. A reservoir assembly can include a restrictor and a reservoir.

A reservoir can be any compartment or portion of a compartment suitable for holding $N_2O_4$, $NO_2$ or NO, or other compounds which can generate $N_2O_4$, $NO_2$ or NO. The reservoir can hold a liquid or a solid, but preferably the reservoir can hold liquid $N_2O_4$. The reservoir can be made of any material, which does not react with or adsorb $N_2O_4$, $NO_2$ or NO, or other compounds which can generate $N_2O_4$, $NO_2$ or NO. The material should also be able to tolerate heat within the appropriate range, discussed below, and repeated heating and cooling.

A reservoir can include a nitrogen dioxide source. A nitrogen dioxide source can include $N_2O_4$, $NO_2$, or compounds which can generate $NO_2$. Preferably, the nitrogen dioxide source can contain liquid $N_2O_4$. In the case of liquid $N_2O_4$, the amount of liquid $N_2O_4$ in the reservoir can be less than about 5.0 g, less than about 2.0 g, less than about 1.0 g, less than about 0.50 g, less than 0.25 g or less than 0.10 g; the amount of liquid $N_2O_4$ in the reservoir can be greater than about 0.05 g, greater than about 0.10 g, greater than about 0.20 g, greater than about 0.50 g or greater than about 1.0 g. The amount of liquid $N_2O_4$ in the reservoir can be less than about 5 ml, less than about 2 ml, less than about 1 ml, less than about 0.5 ml, less than about 0.25 ml or less than about 0.10 ml; amount of liquid $N_2O_4$ in the reservoir can be greater than about 0.001 ml, greater than about 0.01 ml, greater than about 0.05, greater than about 0.10 ml, greater than about 0.25 ml, greater than about 0.50 ml or greater than about 1.0 ml.

In one exemplary embodiment, liquid $N_2O_4$ can be stored in a small reservoir. For a delivery concentration of 80 parts per million in 1 liter of air per minute, for example, the amount of $N_2O_4$ needed for a 24 hour supply can be approximately 0.24 g, or 0.15 ml. $N_2O_4$ boils at 21° C., so the device should be heated to above this temperature in order to have a vapor pressure of $NO_2$ that is greater than atmospheric pressure. Further description may be found in U.S. Provisional Application Nos. 61/263,332 and 61/300,425, each of which is herein incorporated by reference in its entirety.

A reservoir can also include nitrogen dioxide vapor or gas in a space over the nitrogen dioxide source.

A reservoir can be any size. The size of the reservoir can depend on how the reservoir will be used. It can also be dependent on the amount of the nitrogen dioxide source, the amount of nitrogen dioxide gas required, or the length of the time over which a flow of nitrogen dioxide would be required. A reservoir can be relatively large, for example, greater than 1 foot, greater than 2 feet, greater than 5 feet, or greater than 8 feet in height ($h_3$, FIG. 2). A reservoir can also be relatively small, for example, less than 2 feet, less than 1 foot, less than 6 inches, less than 4 inches, less than 3 inches, less than 2 inches, less than 1 inch, less than 0.5 inch in height ($h_3$, FIG. 2). An assembly can have a size that can accommodate a reservoir and/or additional elements, such as a restrictor. An assembly can be relatively large, for example, greater than 4 inches, greater than 6 inches or greater than 1 foot in internal diameter ($d_3$, FIGS. 2A-B). An assembly can be relatively small, for example, less than 4 inches, less than 2 inches, less than 1 inch, less than 0.75 inch or less than 0.5 inch in internal diameter ($d_3$, FIGS. 2A-B).

A restrictor can be any device which can limit the flow of $NO_2$ from the reservoir. A restrictor can require that there be enough vapour pressure to force the $NO_2$ vapor out of the reservoir and into the restrictor.

The reservoir can include the restrictor. For example, the restrictor can be an orifice. The restrictor can be coupled to the reservoir. For example, the restrictor can include a tube, most preferably, a capillary tube. The capillary tube can be a quartz capillary tube. The capillary tube can be a narrow bore capillary tube, which can allow for simple, reproducible and accurate use, as well as a cost effective solution. A convenient commercially available restrictor can be a narrow bore quartz tubing that can be used for gas chromatography (GC).

A restrictor can include a first end and a second end. In some embodiments, the first end of the restrictor can be coupled to a reservoir and the second end can be sealed or closed. In some embodiments, the second end, which was previously sealed or closed, can be opened, unsealed or include a broken seal. In some embodiments, a restrictor can further include a length corresponding to the distance between the first end and the second end.

A restrictor can have any dimension, so long as the total pressure drop across the restrictor can be appropriate for the flow of $NO_2$ that is required. In some embodiments, the length of the restrictor can be relatively long, for example, greater than 4 inches, greater than 6 inches, greater than 1 foot, greater than 2 feet, greater than 5 feet, greater than 10 feet or greater than 20 feet long. In some embodiments, a restrictor can be relatively short, for example, at least about 0.1 inch, at least about 0.25 inch or at least about 0.5 inch; the length can be at most about 4 inches, at most about 2 inches, at most about 1 inch, or at most about 0.5 inch. Preferably, the restrictor can have a length of about 0.75 inch. In some embodiments, the internal diameter of the restrictor can be relatively large, for example, greater than about 0.100 microns, greater than about 1 microns, greater than about 5 microns, greater than about 10 microns, greater than about 50 microns or greater than about 100 microns. In some embodiments, the internal diameter of the restrictor can be relatively small, for example, at least about 0.001, at least about 0.005 microns or at least about 0.010; the internal diameter can be at most about 0.100 microns, at most about 0.050 microns, at most about 0.025 microns, or at most about 0.010 microns. Preferably, the restrictor can have a diameter of about 0.010 microns.

The amount of material (e.g. nitrogen dioxide) that is forced out of the reservoir at any temperature can be dependent upon the diameter of the restriction. Thus, the two key design variables can be the temperature of the vessel and the diameter and length of the restriction in the top of the vessel. For example, at about 45° C. a tube of 0.010 microns internal diameter and 0.75 inches long was used to provide 80 ppm of $NO_2$ in an air stream of 1 l/min.

The restrictor can be made of other materials known to those of skill in the art. The material should not react with or adsorb $N_2O_4$, $NO_2$ or NO, or other compounds which can generate $N_2O_4$, $NO_2$ or NO. The material should also be able to tolerate heat within the appropriate range, discussed below, and repeated heating and cooling.

A restrictor can be sealed. For example, if the restrictor is made of quartz or glass, one end of the restrictor can be heat sealed or melted to close off the opening on that end of the restrictor. The sealed end of the restrictor can be opened by breaking off the end, which can permit a channel in the restrictor to be fully opened. The restrictor can be bevelled or scored to allow for an easier and cleaner break. A restrictor can also be sealed with a metal seal. A metal seal can be melted, punctured, peeled off or otherwise removed to open the sealed end (i.e. break the seal). A restrictor can include a valve, for example, a micromachined valve. Other suitable seals and methods for controlling or preventing flow are known to those of skill in the art. Once the sealed or closed end is opened, nitrogen dioxide can traverse the length of the restrictor and out the previously closed or sealed end.

Figure 2B:
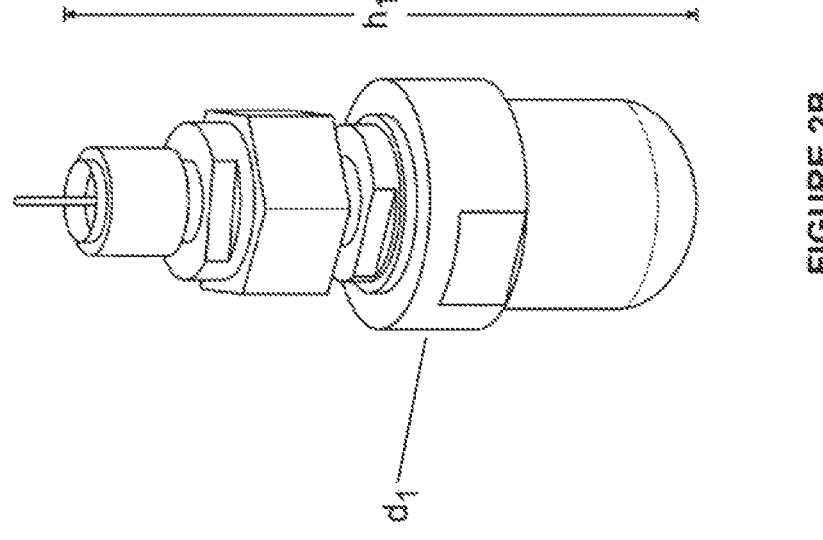
FIGS. 2A and 2B are diagrams of a cartridge.
Figure 2A:
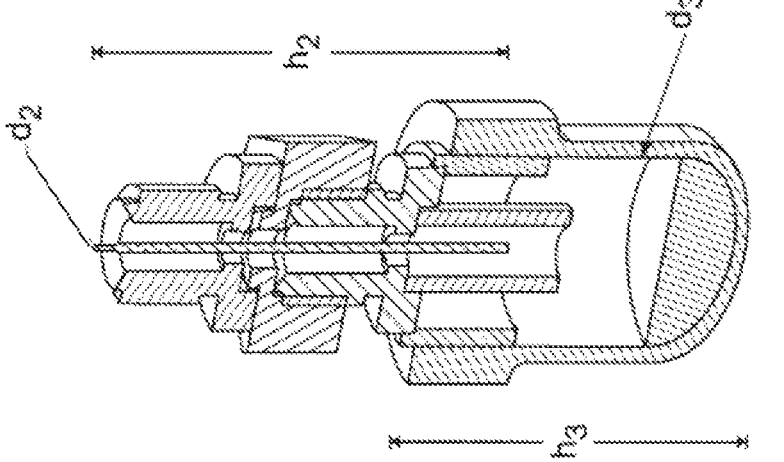

A reservoir assembly including a reservoir and a capillary can be less than 1 foot, less than 6 inches, less than 5 inches, less than 4 inches, less than 3 inches or less than 2 inches in height (hi, FIGS. 2A-B). In an exemplary embodiment, the assembly can be approximately 1.6 inches in height. An assembly can also be less than 1 inch, less than 0.75 inch or less than 0.5 inch in diameter (di, FIGS. 2A-B). In an exemplary embodiment, the assembly can be approximately 0.4 inch (e.g. 0.43 inch) in diameter.

Figure 3:
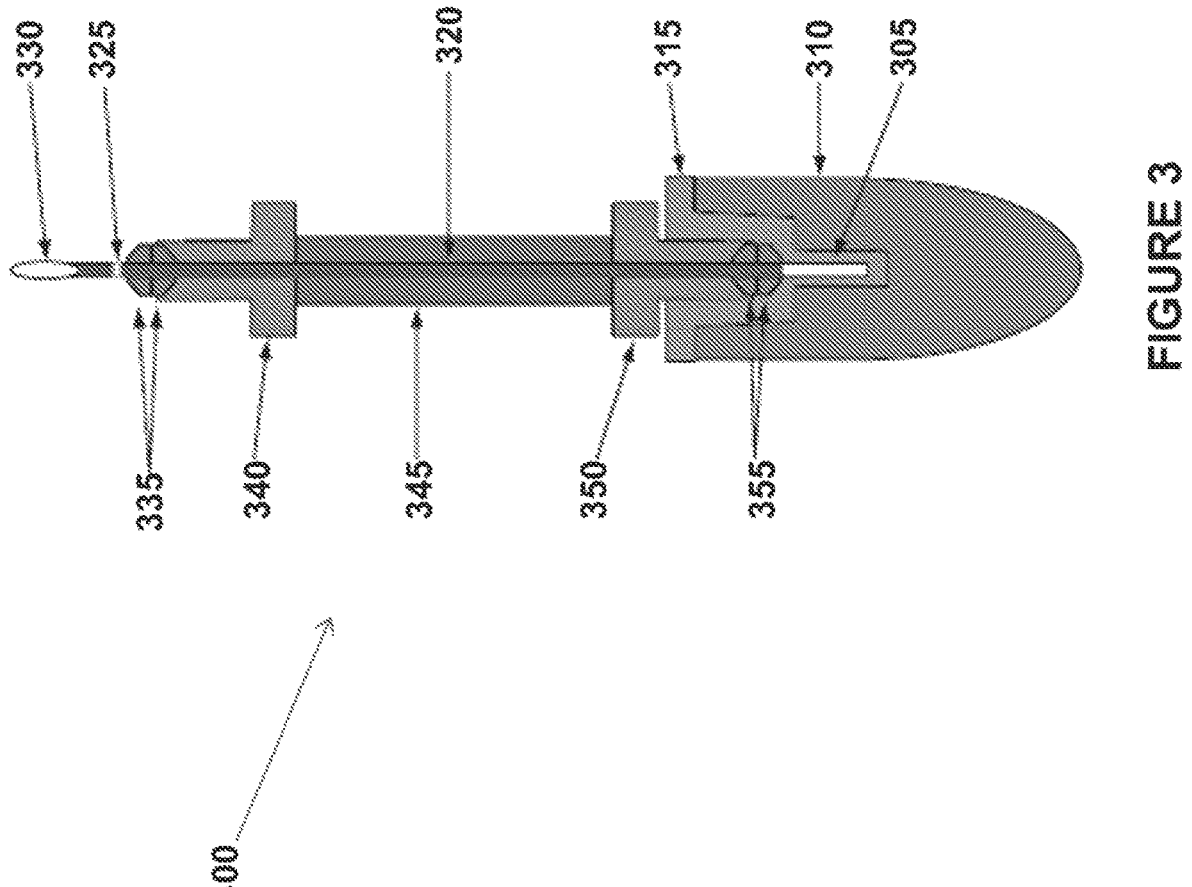
FIG. 3 includes a diagram of a cartridge and a cut-away diagram of a cartridge.

Referring to FIG. 3, in one embodiment of a reservoir assembly, a restrictor can be a capillary 320, which can be about 1-inch×10 um internal diameter (TSPO10375 Flexible Fused Silica Capillary Tubing Polymicro Technologies). The capillary 320 can be inserted through a metal (303 S.S.) tube 345 made up of two GC nuts 340 and 350 ($\frac{1}{16}$" Stainless Steel Nut Valco P/N ZN1-10) connected via their tops to a metal tube 345. Two graphite ferrules 355 (Graphite Ferrules P/N 20227 $\frac{1}{16}$"×0.4 mm Restek) with their flat ends touching can be placed on one end of the capillary 320, which has the polyamide coating 305 removed below the ferrules 355 (e.g., by burning off the polyamide with a flame). The ferrules 355 can hold the capillary 320 securely when the nut 340 is inserted into a separate female end of an adaptor 315, which can be itself inserted into the metal (303 S.S.) reservoir container 310. The adaptor 315 can have a metal sheath 345 on the reservoir end that can cover and protect the area of the capillary without polyamide.

The end 330 of the capillary 320 opposite the reservoir adaptor can be flame sealed and scored. The sealed capillary can be tested with a helium flow to assure that the assembly is appropriately sealed and does not leak. The reservoir container 310 can be filled with liquid $NO_2/N_2O_4$ by distillation or other means. The capillary 320 is attached to the reservoir by means of a $\frac{1}{8}$ inch pipe thread and sealed. The reservoir assembly can be heated and checked to assure that there are no $NO_2$ leaks.

The entire liquid reservoir assembly can be heated. Methods for heating the assembly can include: 1) a hot water bath, 2) a heating mantle that straps onto the tubes, insulating the outside of the metal tubing with urethane or another insulator such as paint, and wrapping Kanthal heating wire around the device, and/or 3) using silver paint to paint the heating element onto top of the insulating paint.

The reservoir assembly 300 can then be attached to the delivery conduit by inserting the sealed end 330 of the capillary 320 with two ferrules 335 (Graphite Ferrules P/N 20227 $\frac{1}{16}$"×0.4 mm Restek) with their flat ends touching and screwing the exposed GC nut 340 of the reservoir assembly into the delivery conduit.

The sealed end 330 of the capillary 320 can be inserted into an off-center hole of the internal delivery seal. When ready to use, the internal delivery seal can be rotated to open the reservoir port to the system flow path, which can break the capillary at its scored end 325, thus opening the reservoir to the system flow path and starting the flow of $NO_2$.

An advantage of having the capillary tube inside the reservoir and protected by the tubing can be that the toxic $N_2O_4$ can only escape through the narrow bore quartz tube.

In order for any material to escape the heater has to be turned on to provide the driving force. The tiny liquid reservoir assembly (FIGS. 2A-B), which can measure, for example, about 1.6 inch in height and 0.43 inches in diameter, can replace a large pressurized gas cylinder, the gas regulator and the gas control valve. The size can be similar to that of a cap for a ball point pen.

The assembly can be kept the $N_2O_4$ frozen solid at dry ice temperatures. However, while this is suitable for laboratory use, it may be impractical as a safe medical delivery device for use with a patient.

Figure 4:
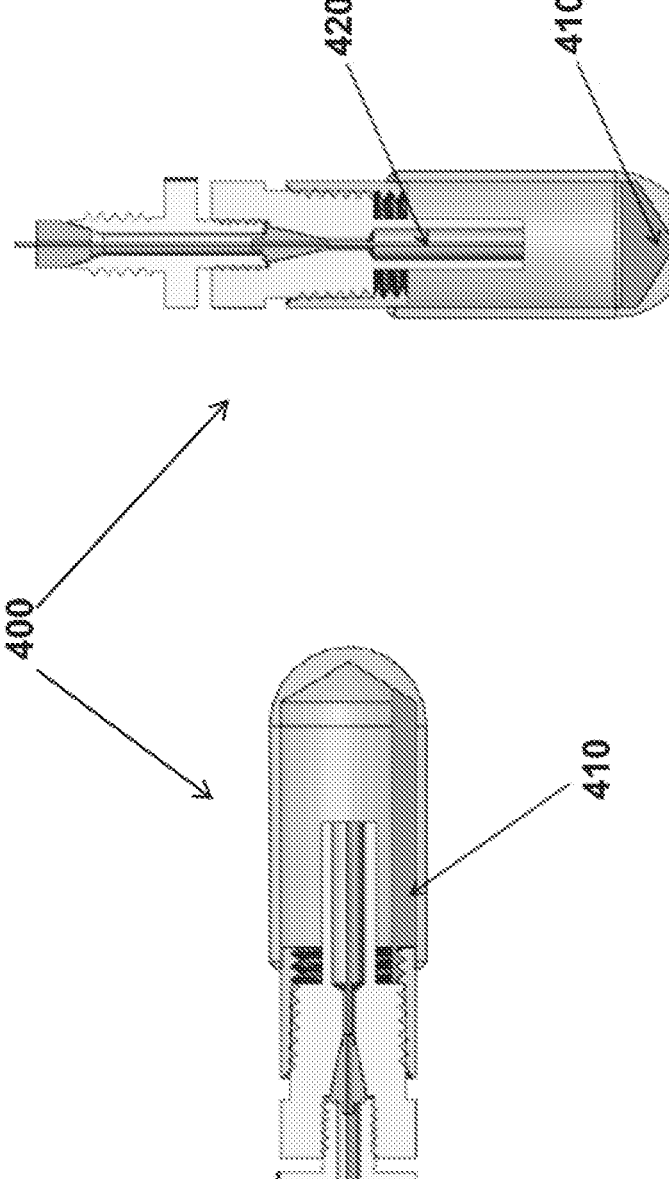
FIG. 4 is a diagram of a cap of a cartridge.

FIG. 4 includes an alternative embodiment. The can include a reduced number of parts, but the overall concept can remain the same. This embodiment can be less expensive to produce. The size and shape of the vessel 400 can be such that the liquid 410 can never enter the restrictor 420, e.g. capillary tube. In FIG. 4, the vessel 400 is on its side, and the liquid level 410 can remain below the level where it could enter the restrictor 420. Similarly, the vessel 400 can be inverted and it can still function. The restrictor 420 can be protected by a wider bore splash guard. A baffle (not shown) can also be placed in front of the restrictor 420 so as to eliminate the possibility of a minute droplet entering the restrictor 420.

Figure 5:
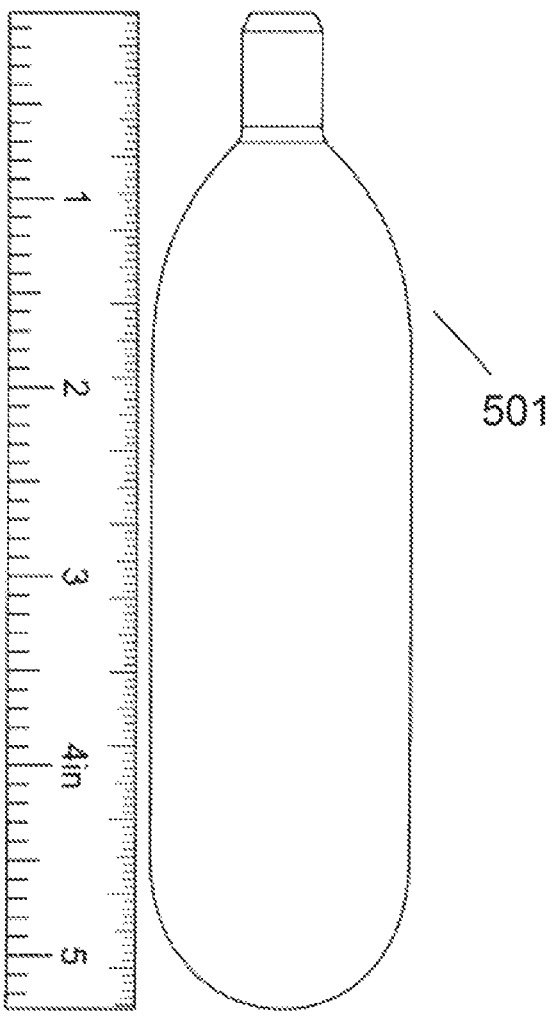
FIG. 5 is a diagram of a system for delivering nitric oxide.

In another embodiment, methods that are used to seal carbon dioxide in metal tubes for a wide variety of commercial and consumer applications can be used (FIG. 5). The liquid $NO_2$ can be sealed inside a steel or aluminum canister, similar to those used for carbon dioxide (see Leland corporation). These devices can have a welded cap made of a thin sheet of steel. The welding can be carried out by resistance heating or other techniques. The advantage of this system can be that the liquid can be sealed inside the container and the containers can be safely shipped. For this application, the volume of the nitrogen dioxide source should be less than 5 ml, less than 2 ml, preferably less than 1 ml. Alternatively, a crimp seal could be used as long as the seal could take the internal pressure of about 100 psi without leaking. The material can be aluminum or stainless steel.

The loading and cap penetration technique can be identical to what is used for carbon dioxide pellet guns and for the multitude of other uses of these tiny high pressure cylinders.

In one aspect, a system for delivering nitric oxide can include a reservoir, a gas supply and a delivery conduit. A system can further include a restrictor. A reservoir and a restrictor have been described above. In some embodiments, a system can include a reservoir and a restrictor, which are part of a reservoir assembly.

A gas supply can be any suitable source of gas, for example air, oxygen or nitrogen. A preferred gas supply is an air supply, for example, an air pump. For the ambulatory platform an air stream can be provided by a small air pump. An air compressor, an external supply of air or oxygen gas from gas bottles can also be used, including oxygen enriched air for a home oxygen generator. The use of air or oxygen, wet or bone dry, may make no difference to performance, as measured by a constant output over time. However, moist air greatly can extend the life of the reducing agent cartridge (e.g. ascorbic acid cartridge) that the $NO_2$ gas will be passed through to generate the drug, nitric oxide. Nevertheless, the platform can be designed for the worst case, which is bone dry air or oxygen.

The system can further include a delivery conduit. A delivery conduit can include a NO sensor, a $NO_2$ sensor, or a temperature sensor. A NO sensor can include a chemiluminescent detector or an electrochemical sensor. A $NO_2$ sensor can include a chemiluminescent detector or an electrochemical sensor. A temperature sensor can include a thermistor or a thermometer. In some instances, the system can include a pressure sensor or a flow sensor. A delivery conduit can also include other medically relevant devices, for example, a filter for eliminating microorganisms prior to inhalation of NO by a patient. It should also be understood that a delivery conduit can include additional hardware, such as tubing and valves, necessary to fluidly communicate gas (e.g. $NO_2$, NO, air, oxygen, nitrogen, etc.) from one element of the system to another.

The delivery conduit can have an inlet, which can be coupled to the gas source. The delivery conduit can also include an outlet, which can be couple to a patient interface. A patient interface can include a mouth piece, nasal cannula, face mask, or fully-sealed face mask.

If the patient required the co-delivery of oxygen, the air feed can be replaced with oxygen, or a dual lumen cannula can flow both the NO in air and oxygen down parallel lumens to the patient, mixing the NO in air line and the oxygen in the nose.

It is also well within the capability of the technology to add an oxygen conserver to the NO output, thereby extending the life time of the disposable component.

The second end of a restrictor can also be coupled to the delivery conduit. The second end of a restrictor can be coupled to the delivery conduit at a location between the inlet and the outlet of the delivery conduit. A restrictor can further include a length corresponding to the distance between the first end and the second end. In some cases, the second end of the restrictor is coupled to the delivery conduit such that the delivery conduit traverses in a direction perpendicular to the length of the restrictor.

As the second end of a restrictor can be closed, the delivery conduit can include a device for opening the second end or breaking the seal on the second end.

A system can further include a GeNO cartridge. The cartridge can employ a surface-active material coated with an aqueous solution of a reducing agent, for example an antioxidant, as a simple and effective mechanism for making the conversion. More particularly, $NO_2$ can be converted to NO by passing the dilute gaseous $NO_2$ over a surface-active material coated with an aqueous solution of a reducing agent, e.g. an antioxidant. As an example, when the aqueous antioxidant is ascorbic acid (that is, vitamin C), the reaction can be quantitative at ambient temperatures.

One example of a surface-active material can be silica gel. Another example of a surface-active material that can be used is cotton. The surface-active material may be or may include a substrate capable of retaining a liquid, for example, water. Another type of surface-active material that has a large surface area that is capable of absorbing moisture also may be used.

Figure 6:
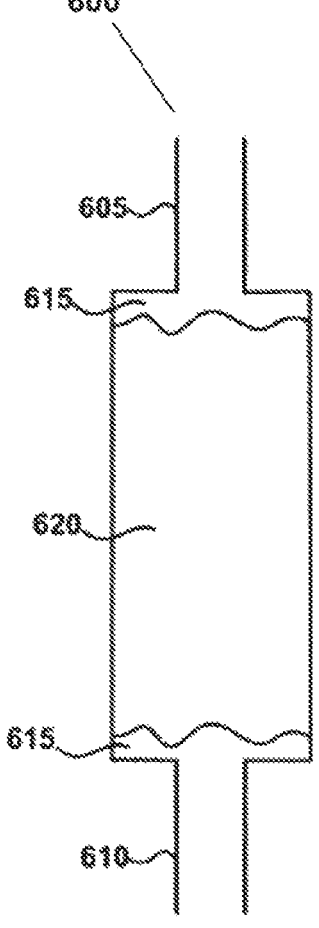
FIG. 6 is a diagram of a system for delivering nitric oxide.

FIG. 6 illustrates a cartridge 600 for generating NO by converting $NO_2$ to NO. The cartridge 600, which may be referred to as a cartridge, a converter, a NO generation cartridge, a GENO cartridge, a GENO cylinder, GENO converter or Nitrosyl™ Primary Cartridge, can include an inlet 605 and an outlet 610. Screen and/or glass wool 615 can be located at the inlet 605 and/or the outlet 610. The remainder of the cartridge 600 can be filled with a surface-active material 620 that is soaked with a saturated solution including a reducing agent to coat the surface-active material. The saturated solution can be, for example, an antioxidant in water. The screen and/or glass wool 615 can also be soaked with the saturated solution before being inserted into the cartridge 600. The antioxidant can be ascorbic acid.

In a general process for converting $NO_2$ to NO, a gas flow (e.g. air flow) having $NO_2$ can be received through the inlet 605. The gas flow can be fluidly communicated to the outlet 610 through the surface-active material 620 coated with the aqueous reducing agent, e.g. antioxidant. As long as the surface-active material 620 remains moist and the reducing agent may not been used up in the conversion, the general process can be effective at converting $NO_2$ to NO at ambient temperature.

The inlet 605 also may receive the air flow having $NO_2$, for example, from source of $NO_2$. A source of $NO_2$ can include a pressurized bottle of $NO_2$, which also may be referred to as a tank of $NO_2$. The inlet 605 also may receive a gas flow with $NO_2$ in nitrogen, air, or oxygen. The conversion can occur over a wide concentration range. Experiments have been carried out at concentrations in a gas including from about 2 ppm $NO_2$ to 100 ppm $NO_2$, and even to over 1000 ppm $NO_2$. In one example, a cartridge that was approximately 6 inches long and had a diameter of 1.5-inches was packed with silica gel that had first been soaked in a saturated aqueous solution of ascorbic acid. The moist silica gel was prepared using ascorbic acid (i.e., vitamin C) designated as A.C.S reagent grade 99.1% pure from Aldrich Chemical Company and silica gel from Fischer Scientific International, Inc., designated as S8 32-1, 40 of Grade of 35 to 70 sized mesh. Other sizes of silica gel also can be effective. For example, silica gel having an eighth-inch diameter could also work.

The silica gel can be moistened with a saturated solution including a reducing agent. For example, a saturated solution of ascorbic acid in water; more specifically, the saturated solution can be a saturated solution that had been prepared by mixing 35% by weight ascorbic acid in water, stirring, and straining the water/ascorbic acid mixture through the silica gel, followed by draining. The conversion of $NO_2$ to NO can proceed well when the silica gel coated with ascorbic acid is moist. The conversion of $NO_2$ to NO may not proceed well in an aqueous solution of ascorbic acid alone.

The cartridge can be filled with the wet silica gel/reducing agent. For example, a cartridge filled with the wet silica gel/ascorbic acid was able to convert 1000 ppm of $NO_2$ in air to NO at a flow rate of 150 ml per minute, quantitatively, non-stop for over 12 days. A wide variety of flow rates and $NO_2$ concentrations have been successfully tested, ranging from only a few ml per minute to flow rates of up to 5,000 ml per minute. Any appropriate reducing agent that can convert $NO_2$ or $N_2O_4$ to NO can be used as determined by a person of skill in the art. For example, the reducing agent can include a hydroquinone, glutathione, and/or one or more reduced metal salts such as Fe(II), Mo(VI), NaI, Ti(III) or Cr(III), thiols, or $NO_2^-$. The reducing agent can be an antioxidant. The antioxidant can be an aqueous solution of an antioxidant. The antioxidant can be ascorbic acid, alpha tocopherol, or gamma tocopherol. Any appropriate antioxidant can be used depending on the activities and properties as determined by a person of skill in the art. The antioxidant can be used dry or wet.

The antioxidant/surface-active material GENO cartridge may be used for inhalation therapy. In one such example, the GENO cartridge can be used as a $NO_2$ scrubber for NO inhalation therapy that delivers NO from a pressurized bottle source. The GENO cartridge can be used to remove any $NO_2$ that chemically forms during inhalation therapy. This GENO cartridge can be used to help ensure that no harmful levels of $NO_2$ are inadvertently inhaled by the patient.

Using the system as an inhaled NO drug delivery device, the $NO_2$ output in air or oxygen can be passed through a GeNO cartridge, which strips out one of the O atoms from the $NO_2$ to produce ultra pure NO.

Figure 7:
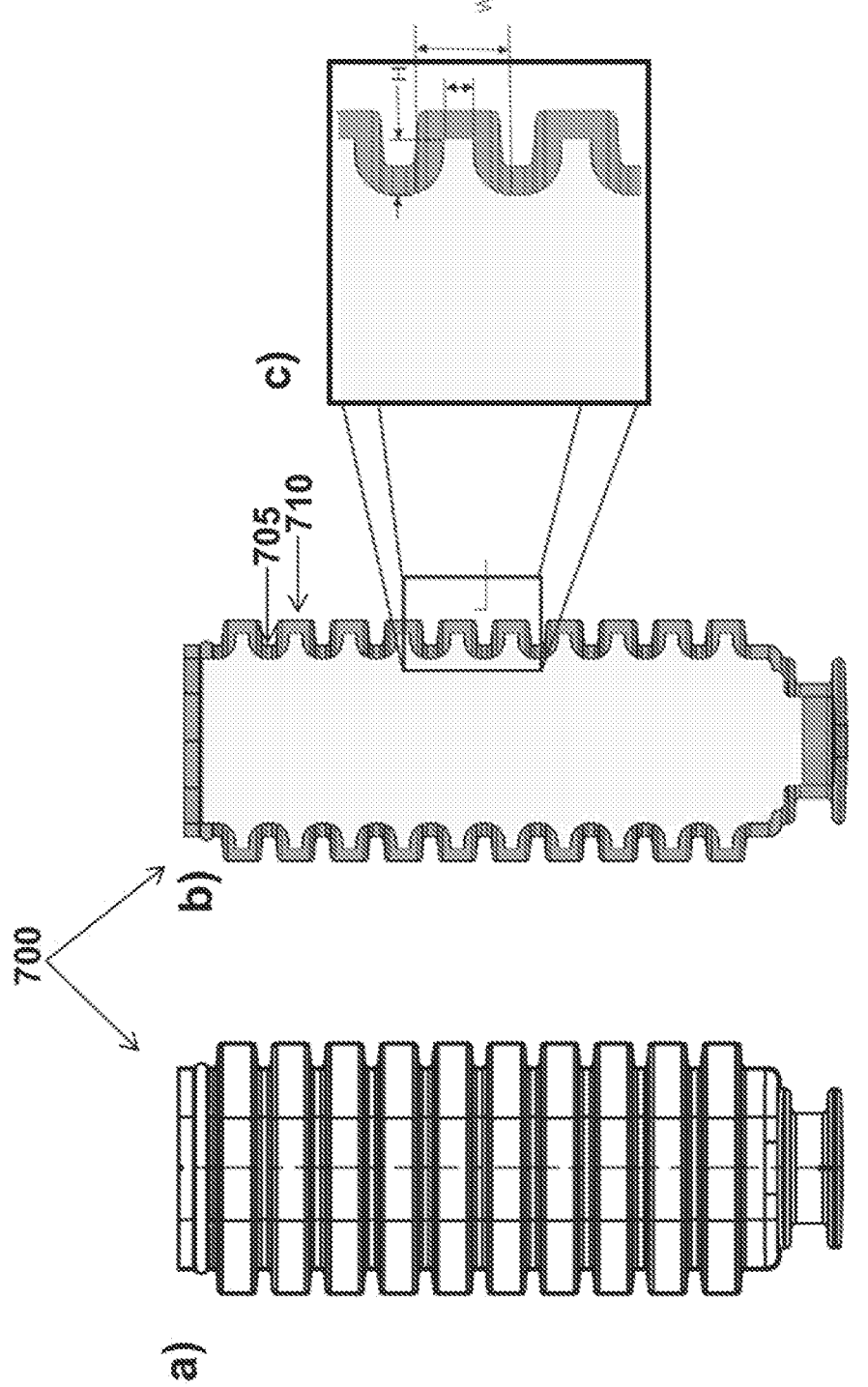
FIG. 7 is an illustration of a reservoir assembly.

Referring to FIG. 7, the cartridges 700 can be blow molded with internal ridges 705 and valleys 710. When packed with the surface active material and reducing agent (e.g. silica gel/ascorbic acid powder), the particles can tend to pack, leaving a small air gap at the top. If the cartridge was allowed to be vibrated on its side, the material could settle. If the tube had a smooth bore, the space above the powder could create a path that bypassed the GeNO converter. By having the ridges 705 and valleys 710, the powder can settle and the vapour cannot have a pathway that would bypass the chemistry reactor. The height of the ridge and its width can be determined by calculation and then confirmed experimentally.

Figure 8:
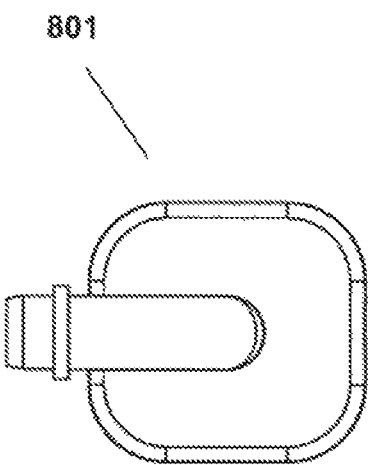
FIG. 8 includes a cut-away of a reservoir assembly and a perspective illustration of a reservoir assembly.

The cap for the cartridges can be molded from plastic (FIG. 8).

Figure 9:
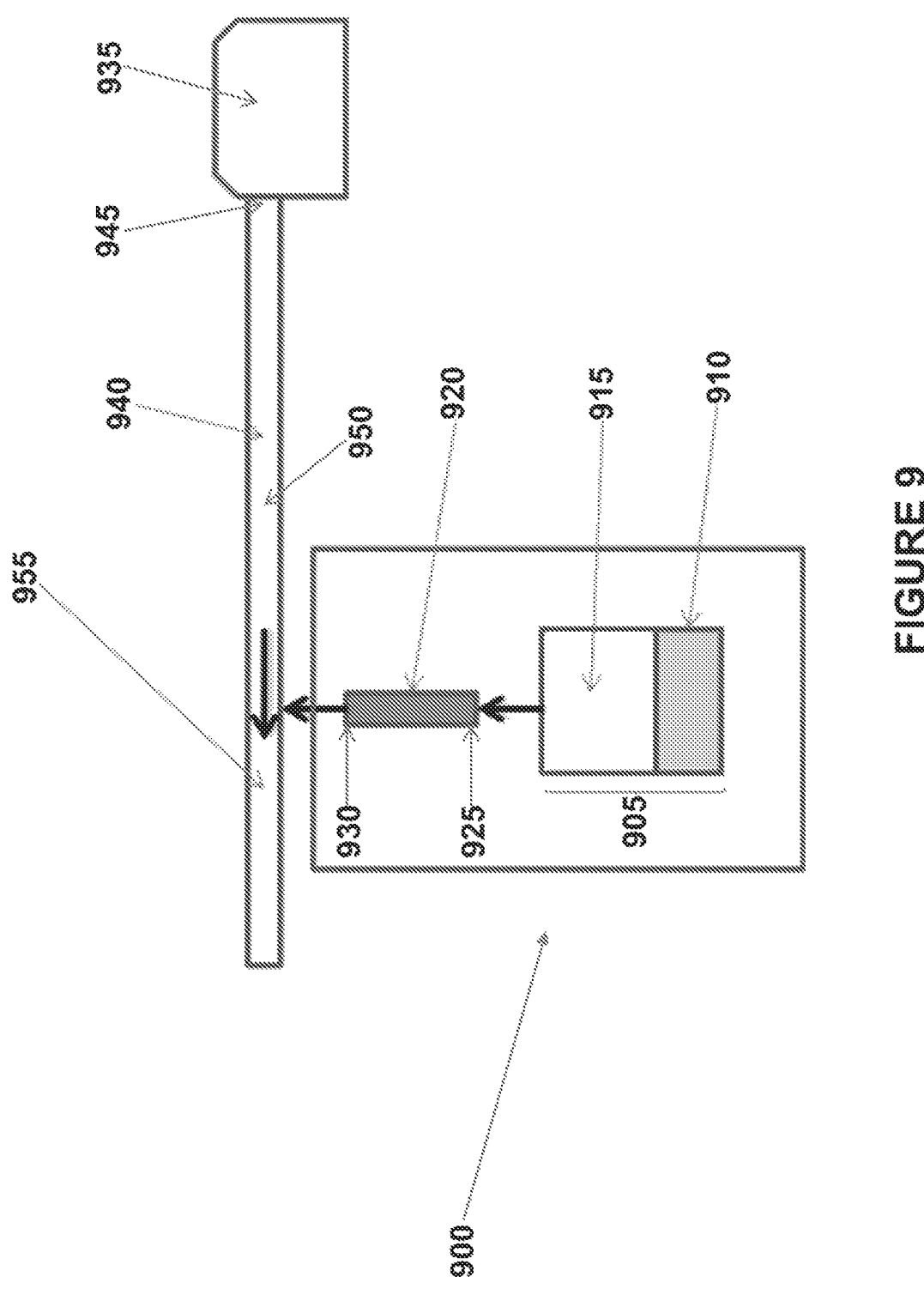
FIG. 9 is an illustration of a reservoir assembly.

An exemplary embodiment of a system is shown in FIG. 9. Referring to FIG. 9, a system 900 can include a reservoir 905. A reservoir 905 can include a nitrogen dioxide source 910, for example, liquid $N_2O_4$. Over the nitrogen dioxide source can be nitrogen dioxide vapor 915. As the vapor pressure of the nitrogen dioxide vapor 915 is increased, for example, by heating the nitrogen dioxide, the nitrogen dioxide vapor 915 can be forced into a restrictor 920. The restrictor 920 can be coupled to the reservoir at a first end 925. The second end of the restrictor 930 can be closed or sealed for storage. To use the system, the second end of the restrictor 930 can be opened or the seal can be broken, which can allow nitrogen dioxide to traverse the length of the restrictor 920 and out the second end of the restrictor 930. A gas supply 935 can provide gas 950, which can traverse through a delivery conduit 940. An inlet 945 of the delivery conduit 940 can be coupled to the gas supply 935. The second end of the restrictor 930 can also be coupled to the delivery conduit 940. In that way, as gas 950 from the gas supply 935 traverses through the delivery conduit 940 and past the second end of the restrictor 930, the gas 950 from the gas supply 935 and the nitrogen dioxide vapor 915 from the reservoir will mix, forming a nitrogen dioxide-gas mixture 955. The nitrogen dioxide-gas mixture can then pass through a number of devices including, but not limited to, sensors, cartridges or filters, as discussed below.

Figure 10:
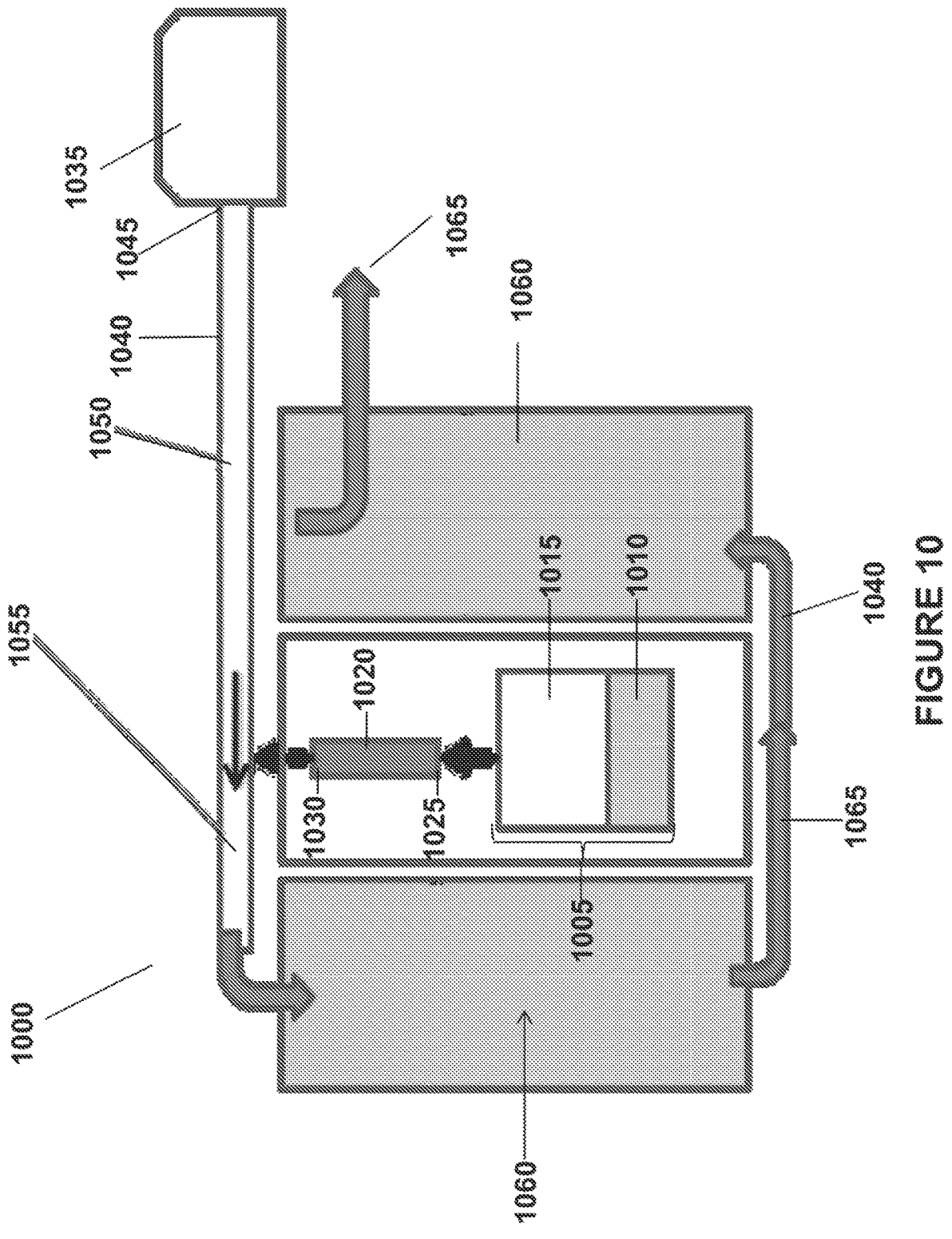
FIG. 10 is a picture of a metal tube.

Another exemplary embodiment of a system is shown in FIG. 10. Referring to FIG. 10, a system 1000 can include a reservoir 1005, which can include a nitrogen dioxide source 1010, for example, liquid $N_2O_4$. Over the nitrogen dioxide source can be nitrogen dioxide vapor 1015. As the vapor pressure of the nitrogen dioxide vapor 1015 is increased, for example, by heating the nitrogen dioxide, the nitrogen dioxide vapor 1015 can be forced into a restrictor 1020. The restrictor 1020 can be coupled to the reservoir 1005 at a first end of the restrictor 1025. The second end of the restrictor 1030 can be closed or sealed for storage. To use the system, the second end of the restrictor 1030 can be opened or the seal can be broken, which can allow nitrogen dioxide to traverse the length of the restrictor 1020 and out the second end of the restrictor 1030. A gas supply 1035 can provide gas 1050, which can traverse through a delivery conduit 1040. An inlet 1045 of the delivery conduit 1040 can be coupled to the gas supply 1035. The second end of the restrictor 1030 can also be coupled to the delivery conduit 1040. In that way, as gas 1050 from the gas supply 1035 traverses through the delivery conduit 1040 and over the second end of the restrictor 1030, the gas 1050 from the gas supply 1035 and the nitrogen dioxide vapor 1015 from the reservoir will mix, forming a nitrogen dioxide-gas mixture 1055. The nitrogen dioxide-gas mixture 1055 can then pass through a first cartridge 1060 included in the delivery conduit. Prior to or following the first cartridge 1060, the nitrogen dioxide-gas mixture 1055 can pass through a number of devices which can include the delivery conduit, including, but not limited to, sensors or filters, as discussed in more detail below. The nitrogen dioxide-gas mixture 1055 can also pass through a second cartridge 1060 prior to exiting the delivery conduit. A patient interface can be coupled to an outlet 1065 of the delivery conduit.

A system can include a heating element. A heating element can be any device that can alter and maintain the temperature of the system, or at least the reservoir and/or the restrictor. The heating element can be a hot water bath, a heating mantle or heating wire. Insulated heating wires can be wrapped directly onto the tube surface. A heated well can also be used. Other suitable examples of a heating element are known to those of skill in the art.

Figure 11:
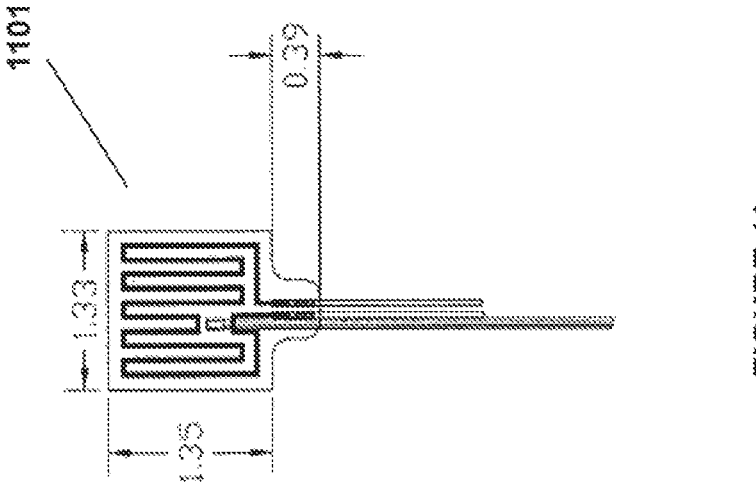
FIG. 11 is diagram of a circuit board.

In an exemplary embodiment, the system or a portion of the system, for example the reservoir and/or restrictor, can be heated by means of a simple flexible circuit board with the wires etched onto the surface (FIG. 11). A device including a thermistor can be built into the circuit for measuring and controlling the temperature.

When heating a system or a portion of a system, the lowest temperature that is practical can be about 25° C. However, it can be difficult to control the temperature precisely when it is close to ambient temperature. For maximum control, the temperature should be set to be above the highest possible ambient temperatures. The upper temperature limit can, in principle, be many hundreds of degrees centigrade. A practical limit can be the engineering balance of (a) having the liquid hot enough to develop the pressure that can force the vapor out of the device, and (b) minimizing the amount of energy that may be needed, especially for battery powered devices, minimizing the amount of thermal insulation that may be needed (a size factor) and the complexity of the storage vessel as far as ensuring that it can withstand the pressures that may be developed inside the vessel. The temperature can be at least about 25° C., at least about 30° C., at least about 35° C., at least about 40° C., at least about 45° C. or at least about 50° C.; the temperature can be at most about 200° C., at most about 150° C., at most about 100° C., or at most about 75° C. The optimum temperature range can be about 45 to 75° C., which can develop enough vapor pressure to force the $NO_2$ vapor through the restrictor.

The reservoir and/or the restrictor can be heated. The reservoir and the restrictor can be heated to substantially the same temperatures, for example less than 10° C. difference, less than 5° C. difference, 2° C. difference or less than 1° C. difference between the temperature of the reservoir and the temperature of the restrictor. This can avoid condensation of $NO_2$. Also, the temperature of the system, more specifically, the reservoir and/or the restrictor, can be controlled to better than about 1° C., preferably better than about 0.5° C., in order to maintain a constant output of $NO_2$ vapor. The higher the temperature of the vessel, the better the temperature control should be. This need can come about because the vapor pressure can approximately double with a 10 degree rise in temperature. Thus, for a fixed restrictor and fixed air flow, the concentration of $NO_2$ in the output can double from approximately 40 ppm at 45° C. to 80 ppm at 55° C., to 160 ppm at 65° C. to 320 ppm at 75° C. At 65° C., a 0.5° C. variation in temperature can cause a change in output that is more than 4 times greater than at 45° C.

Figure 12:
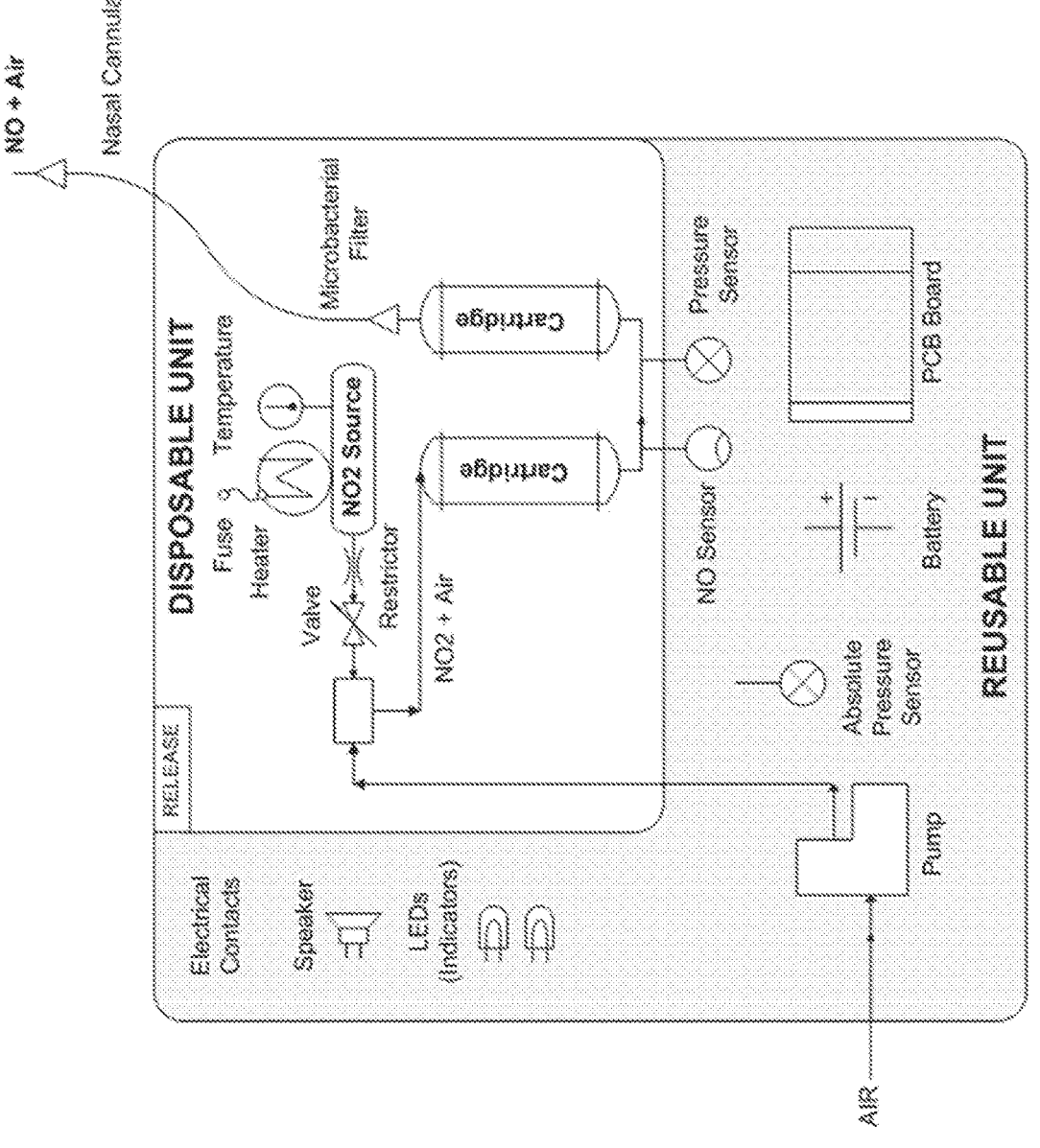
FIG. 12 is a diagram of a system including a disposable module.

In one embodiment, a portion of the system can be reusable and a portion of the system can be disposable. For example, a reusable base unit can include a gas supply (e.g. air pump). A reusable base unit can also include sensors, power supply (e.g. batteries), alarm systems, lights, indicators, and/or electronics (FIG. 12). A disposable unit can include reservoir, the nitrogen dioxide source (e.g. $N_2O_4$ storage vessel), restrictor and/or at least one GeNO cartridge (e.g. two GeNO cartridges). The disposable unit can further include filters, a heating element, and/or sensors. One purpose of the design can be to make the disposable system as low cost as possible, while ensuring safety. The liquid $N_2O_4$ source and the at least one GeNO cartridge can be contained in a sealed unit that can be produced in large quantities. A typical patient can use one disposable unit per day, which can depend upon the size of the reservoir, the amount of the nitrogen dioxide source, the size of the cartridges, and the dose required.

Figure 13:
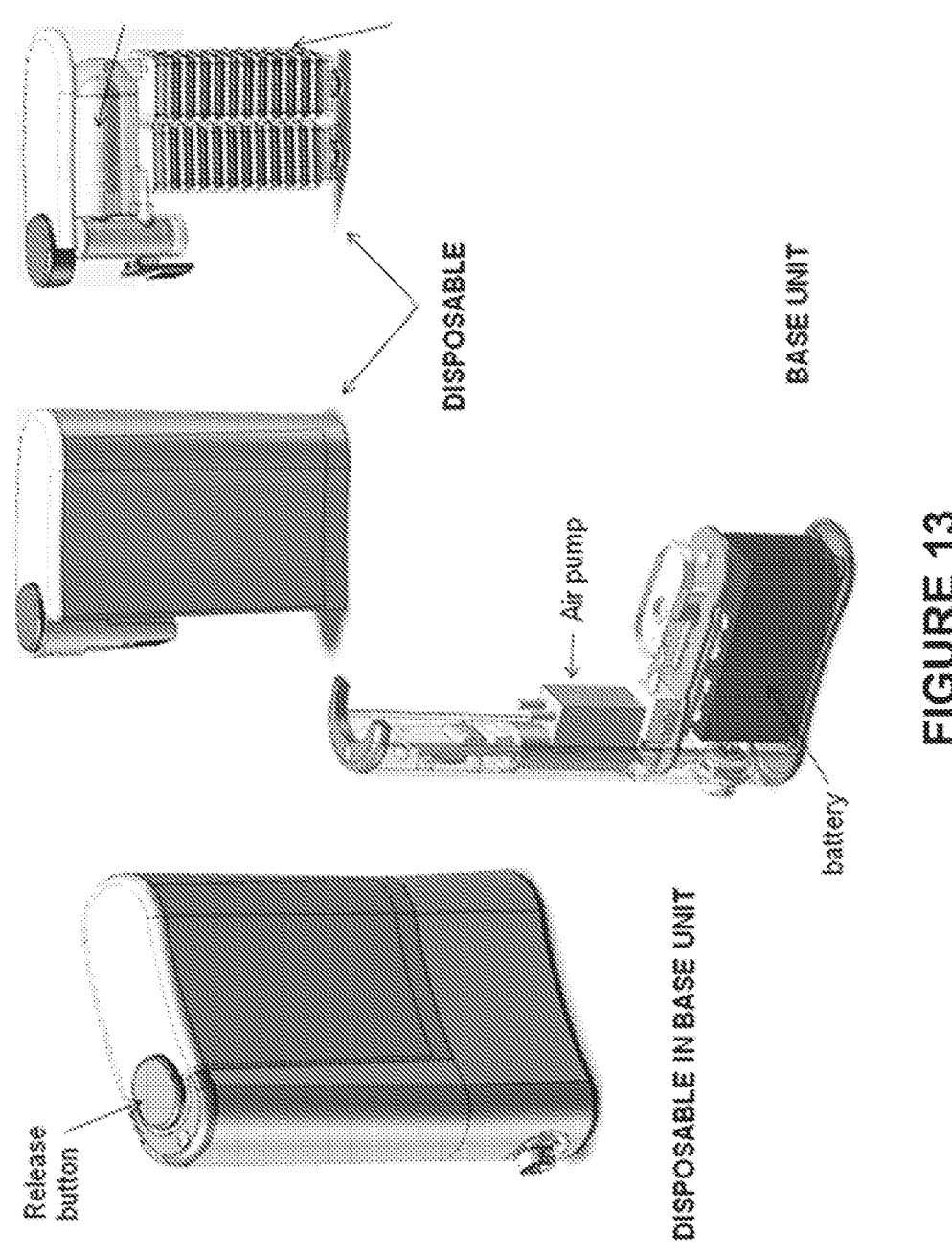
FIG. 13 includes perspective drawings of a system including perspective drawings of a disposable module and a base unit.

In one embodiment, between the two cartridges, the flow path can pass over an NO sensor (P/N NO-D4 Alphasense, Ltd. United Kingdom), which can verify that the NO levels do not exceed or fall below specified levels. If necessary, the sensor can trigger alarms or shut off the gas supply. One embodiment is shown below in FIG. 13, which shows the base and the disposable, separately and combined.

Some of the safety features of the disposable/reusable system can include the following: 1) an activated charcoal filter on the air intake prior to the valve which breaks off the quartz tip, where the charcoal filter could be large enough to adsorb all of the $NO_2$ in the reservoir, 2) a tip enclosed in a sealed Teflon chamber during shipment, which can only be moved by inserting the disposable unit into the base unit, so that even if the glass tip broke the $NO_2$ would be contained; 3) an interlock so that the disposable unit can only be used once; 4) warnings and alarms, including, but not limited to, warning lights for low battery, low or high NO, wrong flow, etc.; 5) an encased liquid reservoir, where the reservoir can be entirely encased in an activated charcoal sheath which will be of sufficient mass to adsorb all of the $NO_2$ in the storage vessel; 6) a thermal fuse on the heater element so that the unit can never exceed its set temperature; and 7) sensors for flow, pressure atmospheric pressure, etc.

Figure 14:
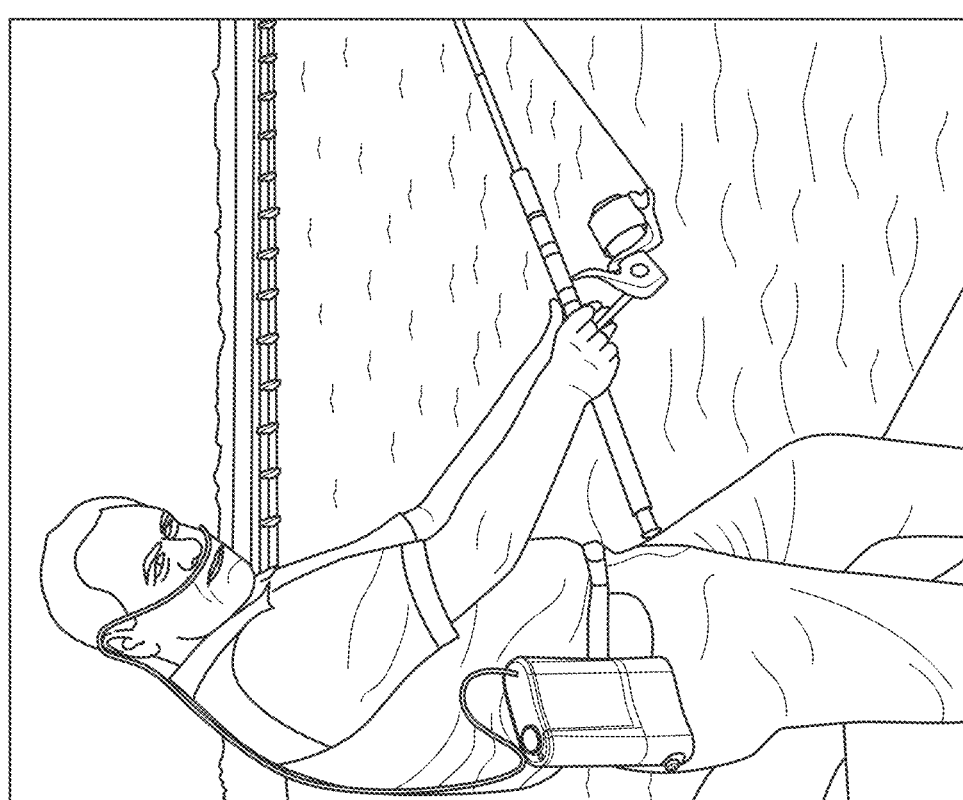
FIG. 14 is a picture of a system in use.

FIG. 14 shows the size of an exemplary device, in which a man is shown wearing the device while fishing. The miniaturization can be an important feature. Current commercially available delivery systems for inhaled NO can require a patient to be confined to a bed in a hospital and usually in an Intensive Care Unit. The ability to supply inhaled NO chronically in a simple fashion represents a breakthrough in treatment with inhaled NO.

A system can be relatively small. The system can weigh less than 64 ounces, less than 32 ounces or less than 16 ounces. The system can be less than 2 feet, less than 1.5 feet, less than 1 foot in height. The system can be less than 2 feet, less than 1.5 feet, less than 1 foot, less than 9 inches or less than 6 inches in width. The system can be less than 6 inches, less than 4 inches, less than 3 inches or less than 2 inches in depth.

A method of for delivering nitric oxide can include breaking the seal on a second end or opening a closed second end of a restrictor. The restrictor can have a first end in a reservoir containing a nitrogen dioxide source. The method can also include heating the reservoir and the restrictor, which can also heat the nitrogen dioxide source in the reservoir and nitrogen dioxide gas in the reservoir and/or the restrictor. As the nitrogen dioxide gas is heated, vapor pressure can accumulate within the reservoir, releasing the nitrogen dioxide gas into the restrictor. Once the second end is opened or unsealed, nitrogen dioxide gas that is forced into the restrictor can pass through the second end of the restrictor. The method can further include passing a gas from a gas supply across a second end of a restrictor. Passing gas from a gas supply across the second end of a restrictor can create negative pressure at the second end of the restrictor. The increased vapor pressure in the reservoir and/or the negative pressure at the second end of the restrictor can force $NO_2$ vapor through the restrictor. This can result in the $NO_2$ gas mixing with the gas from the gas supply. The $NO_2$ gas mixed with the gas from the gas supply can then be passed through at least one GeNO converter. Additionally, a method can include monitoring the level of NO with a NO sensor, monitoring the level of $NO_2$ with a $NO_2$ sensor, or monitoring the temperature with a temperature sensor.

In one example, the system is activated by breaking the seal of a sealed restrictor, for example, breaking off the tip of a quartz capillary restrictor tube. $NO_2$ vapor can be expelled from the reservoir at a constant flow rate, which can be dependent on the availability of liquid in the reservoir and the temperature of the reservoir. The $NO_2$ vapor can mix with gas, e.g. air, from a small pump and the dilute $NO_2$ mixture can then be allowed to pass through a first GeNO converter, where the $NO_2$ can be converted into NO. The converter can be made up of fine silica gel soaked in a reducing agent, e.g. ascorbic acid solution, and then partially dried. The NO in gas stream can be flowed to the second GeNO converter. A second GeNO converter can provides double redundancy. Each of the two cartridges can have sufficient silica gel-ascorbic acid powder to convert 1.5 times the content of the liquid in the reservoir. Also, each cartridge can be manufactured from a different lot. The NO in gas stream can be passed across an optional NO, an optional $NO_2$ electrochemical sensor, an optional pressure and/or optional flow sensor. The NO vapor in air can then be delivered to a patient by means of a nasal cannula.

For home use, patients can use a system that delivers a fixed output per unit time. A patient needing a high dose can be provided with a modified system in which increased output can be achieved either by increasing the temperature of the reservoir, changing the diameter of the restrictor or length of the restrictor.

In a hospital setting, the nurse may have a need to vary both the flow rate of air and the gas concentration. This can be accomplished by varying the temperature of the reservoir for increase the output of the reservoir. The air flow can be adjusted, either from a compressor or from increasing the power of a small built in air pump. A system with variable flow and variable output can include a monitor and display of the flow rate and the NO concentration.

EXAMPLES

Example 1

Figure 15:
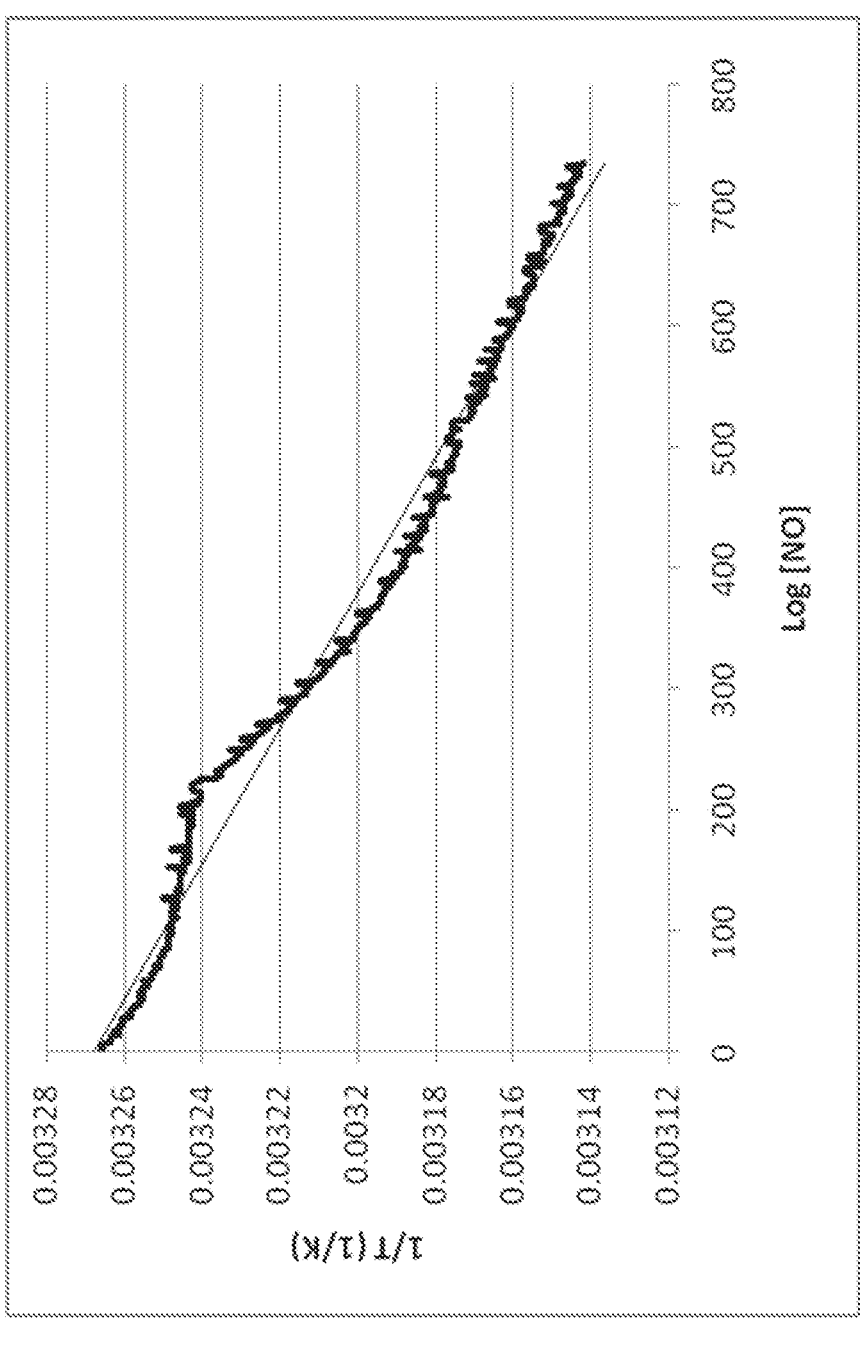
FIG. 15 is a graph of performance data.

The slope of the plot of log (NO) versus 1/T, where T is the absolute temperature, should be a straight line. A typical plot obtained using a nitric oxide delivery system is shown in FIG. 15. The small variation from linearity may due to experimental error due primarily to inadequate temperature control. The flow rate was 1 liter per minute of air.

Example 2

Figure 16:
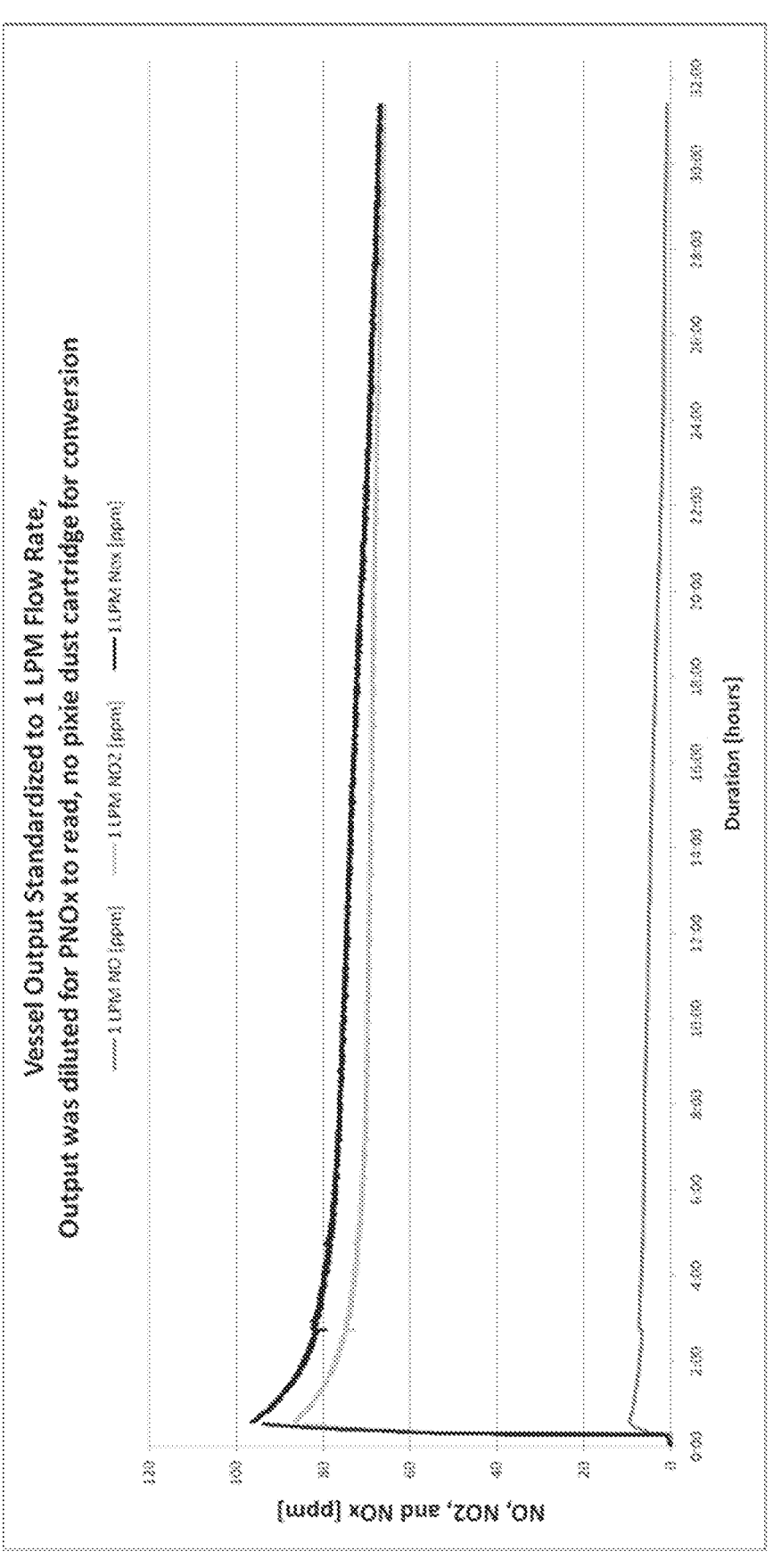
FIG. 16 is a graph of ppm NO, NO$_2$ and NO+NO$_2$ versus time.

The nitric oxide delivery systems can be operated for many days on end without significant variation or degradation. For example, a typical plot of ppm NO, $NO_2$ and $NO+NO_2$ versus time is shown in FIG. 16 for one experiment over a period of about 36 hours. In this experiment the $NO_2$ to NO conversion cartridge was absent. It shows the output of the reservoir, showing the NO level (green line), the $NO_2$ level (yellow line) and the $NO+NO_2$ response (black line) with time in minutes. Without being held to any theory, the initial spike was likely due to the approximately 1% NO impurity that is sometimes added to $N_2O_4$ to reduce corrosion cracking during its conventional use as a rocket fuel oxidiser. Because it has a higher vapor pressure, the NO will de-gas from the liquid in the early stages oxidiser.

Example 3

Figure 17:
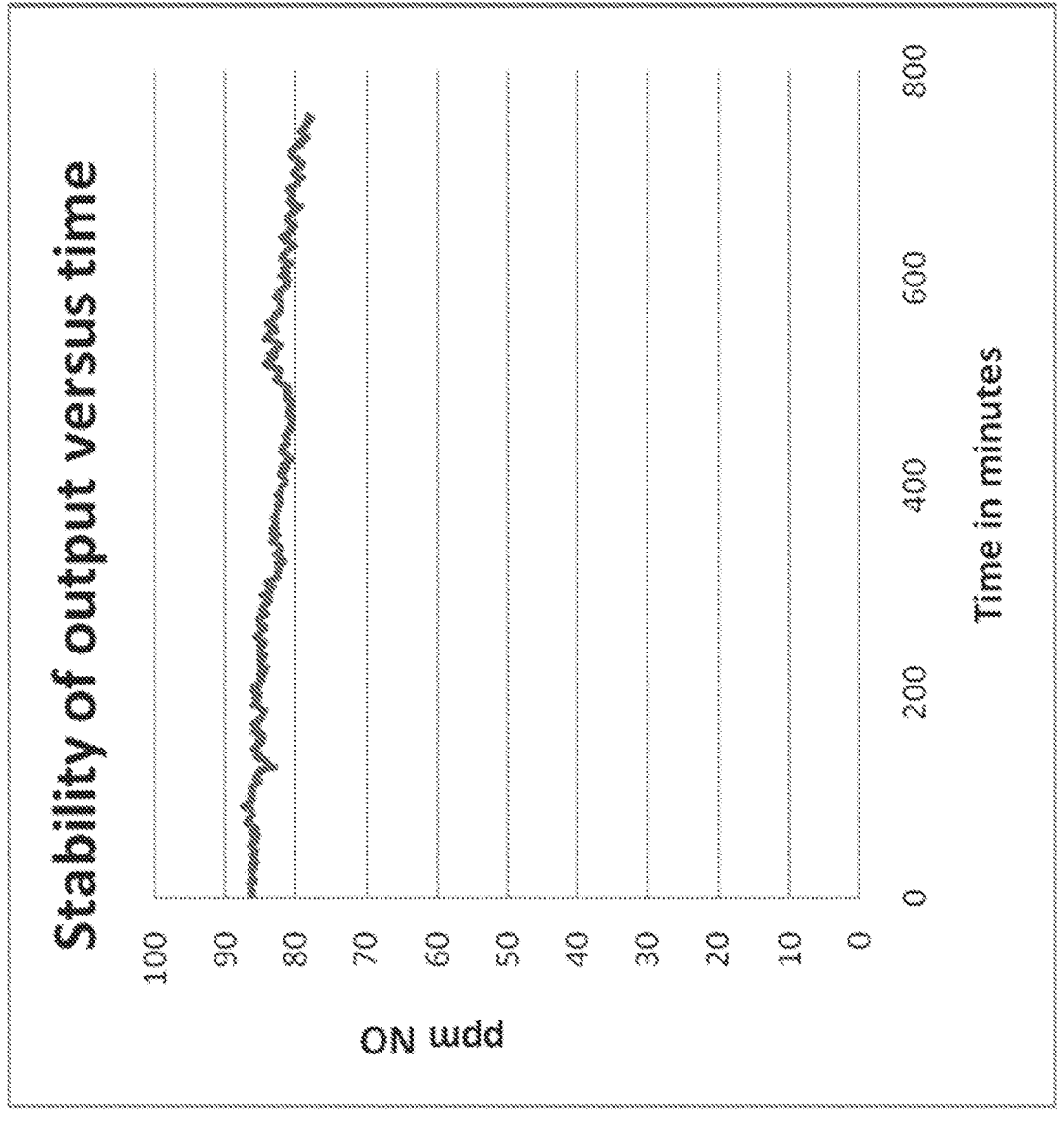
FIG. 17 is a graph of stability of output versus time.

FIG. 17 shows the output when the NO conversion cartridges were included in the system to convert the $NO_2$. In this experiment, the data was collected for 780 minutes (13 hours). While the data shows some drift, it was well within the ±20% that is required for clinical use.

Example 4

Figure 18:
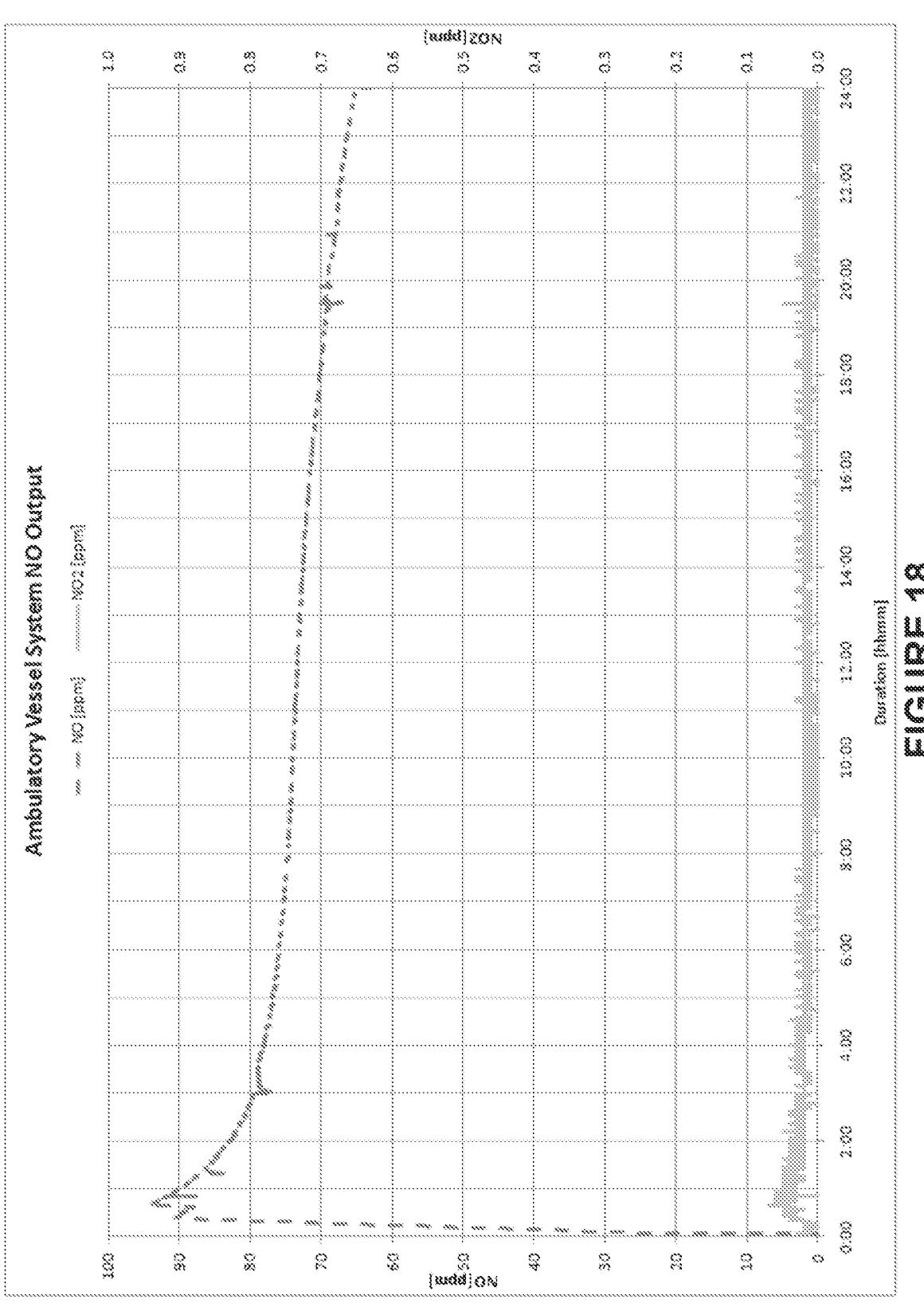
FIG. 18 is a graph of NO and NO$_2$ output over a period of time.

FIG. 18 shows the NO and $NO_2$ output for a period of 24 hours. The $NO_2$ concentration after the gas flow was passed through the cartridges was essentially zero.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed:

1. A disposable module comprising:
   a restrictor connected to a reservoir comprising a source of nitrogen dioxide gas, wherein the restrictor has a dimension defined by a total pressure drop effective to provide a predetermined amount of nitrogen dioxide gas; and wherein the restrictor and the reservoir are configured to be heated to a temperature of at most 200° C., and
   at least one cartridge configured to receive the predetermined amount of nitrogen dioxide gas through the restrictor and to form a therapeutic amount of nitric oxide.

2. The disposable module of claim 1, wherein the restrictor is a capillary tube.

3. The disposable module of claim 1, wherein the restrictor is coupled to the at least one cartridge through a delivery conduit.

4. The disposable module of claim 3, wherein the predetermined amount of nitrogen dioxide received by the at least one cartridge is mixed with a gas.

5. The disposable module of claim 4, wherein the gas is delivered from a gas supply.

6. The disposable module of claim 5, wherein the gas supply is coupled to the delivery conduit.

7. The disposable module of claim 1, wherein the at least one cartridge comprises a surface-active material and a reducing agent.

8. A system comprising a disposable module of claim 1 and a base unit.

9. The system of claim 8, wherein the base unit comprises a gas supply.

10. The system of claim 8, wherein the base unit comprises one or more of batteries, sensors and/or alarm electronics.

11. The system of claim 8, wherein the system is portable.

12. A method, comprising:
   heating to a temperature of at most 200° C. a reservoir comprising a source of nitrogen dioxide to form the nitrogen dioxide;
   passing a predetermined amount of nitrogen dioxide through a restrictor to at least one cartridge, wherein the predetermined amount of nitrogen dioxide is defined by the restrictor's dimension; and
   forming a therapeutic amount of nitrogen oxide in the at least one cartridge.

13. The method of claim 12, forming a gas mixture by mixing the predetermined amount of nitrogen dioxide with a gas from a gas supply in a delivery conduit prior to entering the at least one cartridge.

14. The method of claim 13, wherein the therapeutic amount of nitric oxide is formed by flowing the gas mixture through at least one cartridge, wherein the at least one cartridge comprises a surface-activated material and a reducing agent.

15. The method of claim 14, delivering the therapeutic amount of nitrogen oxide to a patient.

* * * * *